US012623922B2

(12) United States Patent
Dolgopolov et al.

(10) Patent No.: US 12,623,922 B2
(45) Date of Patent: May 12, 2026

(54) DEVICE AND METHOD FOR TREATING LIQUID

(71) Applicant: Millisecond Technologies Corp., New York, NY (US)

(72) Inventors: Dmitry Dolgopolov, Moscow (RU); Phillip R. Frechette, Toa Baja, PR (US); Nikolay Arofikin, Moscow (RU)

(73) Assignee: Millisecond Technologies Corp., New York, NY (US)

(*) Notice: Subject to any disclaimer, the term of this patent is extended or adjusted under 35 U.S.C. 154(b) by 1088 days.

(21) Appl. No.: 17/411,043

(22) Filed: Aug. 24, 2021

(65) Prior Publication Data

US 2021/0387866 A1    Dec. 16, 2021

Related U.S. Application Data

(63) Continuation-in-part of application No. 17/263,861, filed as application No. PCT/US2018/048008 on (Continued)

(30) Foreign Application Priority Data

Jul. 27, 2018    (RU) ........................... RU2018127700

(51) Int. Cl.
C02F 1/02          (2023.01)
A61L 2/00          (2006.01)

(52) U.S. Cl.
CPC .............. C02F 1/02 (2013.01); A61L 2/0023 (2013.01); A61L 2202/22 (2013.01); (Continued)

(58) Field of Classification Search
CPC ...... A61L 2/0023; A61L 2202/22; C02F 1/02; C02F 2209/02; C02F 2209/03; (Continued)

(56) References Cited

U.S. PATENT DOCUMENTS 1,711,097 A        4/1929  Kratzer
1,819,023 A  *     8/1931  Grindrod ................. A23B 2/48
                                                         99/453

(Continued)

FOREIGN PATENT DOCUMENTS

CA        2594134        3/2015
CN        2031204 U      1/1989

(Continued)

OTHER PUBLICATIONS

Belford, "University of Arkansas at Little Rock: Chem 1403 General Chemistry II" textbook, Chapter 13.4, "Pressure and Temperature Effects on Solubility" (Year: 2023).*

(Continued)

*Primary Examiner* — Jennifer Wecker
*Assistant Examiner* — Brady C Pilsbury
(74) *Attorney, Agent, or Firm* — Snell & Wilmer L.L.P.

(57)                    ABSTRACT

Methods and devices use one or more of pressure, pressure drop, increased temperature, rate of temperature increase, and inert gas to kill microbes. Utilizing a method or device, liquid is subjected to a pressure drop and heated either during and/or after the pressure drop. The liquid may be heated while in droplet phase, in a liquid volume, or both. Inert gas may be dissolved into the liquid at a pressure greater than 1 Bar. The pressure is later reduced, which causes inert gas to be released from the liquid. Other method steps and processes are also disclosed.

26 Claims, 10 Drawing Sheets

Related U.S. Application Data

Aug. 24, 2018, application No. 17/411,043 is a continuation-in-part of application No. 15/567,594, filed as application No. PCT/US2016/029045 on Apr. 22, 2016, now Pat. No. 11,096,406.

(60) Provisional application No. 62/209,039, filed on Aug. 24, 2015, provisional application No. 62/152,689, filed on Apr. 24, 2015.

(52) U.S. Cl.
CPC ...... *C02F 2209/02* (2013.01); *C02F 2209/03* (2013.01); *C02F 2301/063* (2013.01); *C02F 2303/04* (2013.01)

(58) Field of Classification Search
CPC ............ C02F 2301/063; C02F 2303/03; C02F 2303/26; A23L 3/015; A23L 3/0155
See application file for complete search history.

(56) References Cited

U.S. PATENT DOCUMENTS

| | | | |
|---|---|---|---|
| 2,052,967 | A | 9/1936 | Fredrik |
| 2,374,805 | A | 5/1945 | Camelford |
| 2,944,479 | A | 7/1960 | Walsh et al. |
| 4,776,268 | A | 10/1988 | Bronnert |
| 4,787,304 | A | 11/1988 | Bronnert |
| 5,092,230 | A | 3/1992 | Bronnert |
| 5,232,726 | A | 8/1993 | Clark et al. |
| 5,914,255 | A | 6/1999 | Grae |
| 6,251,341 | B1 | 6/2001 | Zimmer |
| 6,471,914 | B2 | 10/2002 | Platz et al. |
| 6,736,966 | B2 | 5/2004 | Herrington et al. |
| 6,749,809 | B2 | 6/2004 | Karasawa |
| 7,708,941 | B2 | 5/2010 | Arofikin |
| 8,449,820 | B2 | 5/2013 | Volkov et al. |
| 9,821,994 | B2 | 11/2017 | McIntyre et al. |
| 10,194,680 | B2 | 2/2019 | Arofikin |
| 2001/0038806 | A1 | 11/2001 | Herrington et al. |
| 2002/0020675 | A1 | 2/2002 | Aksenov et al. |
| 2002/0122860 | A1* | 9/2002 | Wildasin ............... A23L 3/3418 426/521 |
| 2003/0035752 | A1* | 2/2003 | Aksenov .................. A23B 2/05 422/26 |
| 2004/0161363 | A1 | 8/2004 | Volkov |
| 2004/0170731 | A1 | 9/2004 | Subramaniam |
| 2006/0199258 | A1 | 9/2006 | Aksenov et al. |
| 2010/0322821 | A1 | 12/2010 | Volkov |
| 2011/0171353 | A1 | 7/2011 | Garwood |
| 2013/0302211 | A1 | 11/2013 | Volkov et al. |
| 2014/0261017 | A1 | 9/2014 | Arofikin |
| 2016/0278413 | A1 | 9/2016 | Van Den Brenk et al. |
| 2017/0265500 | A1* | 9/2017 | Duarte Vieira ........... A23L 2/42 |
| 2018/0092385 | A1 | 4/2018 | Arofikin |
| 2019/0124954 | A1 | 5/2019 | Arofikin |

FOREIGN PATENT DOCUMENTS

| | | |
|---|---|---|
| CN | 1166124 A | 11/1997 |
| CN | 201888207 U | 7/2011 |
| CN | 107787188 | 3/2018 |
| FR | 2735039 | 12/1996 |
| GB | 413460 | 7/1934 |
| IL | 184161 | 3/2012 |
| JP | S56-64771 | 3/1986 |
| JP | 01097459 | 4/1989 |
| JP | 2001346515 | 12/2001 |
| NZ | 707324 | 10/2018 |
| SU | 1745190 | 7/1992 |
| WO | 199732483 | 9/1997 |
| WO | 200056161 | 9/2000 |
| WO | 2001013772 | 3/2001 |
| WO | 2005042219 | 5/2005 |
| WO | 2007008618 | 1/2007 |
| WO | 2011143731 | 11/2011 |
| WO | 2014160020 | 10/2014 |
| WO | 2016172627 | 10/2016 |

OTHER PUBLICATIONS

Haywood, "Thermodynamic Tables in SI (Metric) Units", Cambridge University Press, 1968 (Year: 1968).*

WIPO; Written Opinion dated Apr. 26, 2006 in Int'l. Appl. No. PCT/IB2005/003879.

WIPO; International Search Report dated Apr. 28, 2006 in Int'l. Appl. No. PCT/IB2005/003879.

WIPO; International Preliminary Report on Patentability dated Jun. 26, 2007 in Int'l. Appl. No. PCT/IB2005/003879.

USPTO; Office Action dated Jun. 27, 2008 in U.S. Appl. No. 11/821,216.

USPTO; Office Action dated Feb. 19, 2009 in U.S. Appl. No. 11/821,216.

USPTO; Notice of Allowance dated Oct. 16, 2009 in U.S. Appl. No. 11/821,216.

SIPO; Office Action dated Mar. 3, 2010 in CN Application No. 200580048538.9.

USPTO; Notice of Allowance dated Jan. 28, 2010 in U.S. Appl. No. 11/821,216.

USPTO; Office Action dated Sep. 30, 2010 in U.S. Appl. No. 12/772,610.

ILPO; Office Action dated Jan. 25, 2011 in IL Application No. 184,161.

USPTO; Office Action dated Jun. 30, 2011 in U.S. Appl. No. 12/772,610.

SIPO; Office Action dated Jul. 6, 2011 in CN Application No. 200580048538.9.

SIPO; Office Action dated Dec. 13, 2011 in CN Application No. 200580048538.9.

USPTO; Office Action dated Dec. 29, 2011 in U.S. Appl. No. 12/772,610.

CIPO; Office Action dated May 3, 2012 in CA Application No. 2,594,134.

SIPO; Office Action dated Aug. 31, 2012 in CN Application No. 200580048538.9.

USPTO; Office Action dated Sep. 12, 2012 in U.S. Appl. No. 12/772,610.

SIPO; Office Action dated Jan. 5, 2013 in CN Application No. 200580048538.9.

USPTO; Notice of Allowance dated Jan. 24, 2013 in U.S. Appl. No. 12/772,610.

CIPO; Office Action dated Jan. 30, 2013 in CA Application No. 2,594,134.

SIPO; Notice on Grant of Patent Right for Invention dated Jul. 4, 2013 in CN Application No. 200580048538.9.

USPTO; Restriction Requirement dated Oct. 15, 2013 in U.S. Appl. No. 13/826,856.

USPTO; Office Action dated Jan. 14, 2014 in U.S. Appl. No. 13/826,856.

USPTO; Final Office Action dated Jun. 23, 2014 in U.S. Appl. No. 13/826,856.

USPTO; Office Action dated Nov. 4, 2014 in U.S. Appl. No. 13/826,856.

USPTO; Restriction Requirement dated Feb. 20, 2015 in U.S. Appl. No. 13/800,100.

WIPO; Written Opinion and International Search Report dated Mar. 20, 2015 in Int'l. Appl. No. PCT/US2014/025637.

USPTO; Final Office Action dated Apr. 9, 2015 in U.S. Appl. No. 13/826,856.

USPTO; Office Action dated May 27, 2015 in U.S. Appl. No. 13/800,100.

USPTO; Final Office Action dated Sep. 21, 2015 in U.S. Appl. No. 13/800,100.

USPTO; Advisory Action dated Nov. 30, 2015 in U.S. Appl. No. 13/800,100.

(56)                    References Cited

OTHER PUBLICATIONS

WIPO; International Preliminary Report on Patentability dated Apr. 22, 2016 in Int'l. Appl. No. PCT/US2016/029045.
WIPO; International Search Report dated Apr. 22, 2016 in Int'l. Appl. No. PCT/US2016/029045.
WIPO; Written Opinion dated Apr. 22, 2016 in Int'l. Appl. No. PCT/US2016/029045.
USPTO; Office Action dated Apr. 27, 2016 in U.S. Appl. No. 13/800,100.
USPTO; Final Office Action dated Sep. 15, 2016 in U.S. Appl. No. 13/800,100.
IPAU; Office Action dated Jun. 15, 2017 in AU Application No. 2014244186.
IPONZ; Office Action dated Jun. 2, 2017 in NZ Application No. 707324.
IPONZ; Office Action dated Aug. 16, 2017 in NZ Application No. 707324.
SIPO; Office Action dated Oct. 18, 2017 in CN Application No. 201480026887.
SIPO; Office Action dated Apr. 11, 2018 in CN Application No. 201480026887.
EPO; Office Action dated Apr. 23, 2018 in EP Application No. 14724546.8.
JPO; Office Action dated Jun. 13, 2018 in JP Application No. 201601927.
IPAU; Notice of Allowance dated Jun. 13, 2018 in AU Application No. 2014244186.
USPTO; Notice of Allowance dated Oct. 3, 2018 in U.S. Appl. No. 13/800,100.
SIPO; Office Action dated Jan. 14, 2019 in CN Application No. 201480026887.
ILPO; Office Action dated Mar. 6, 2019 in IL Application No. 241189.
JPO; Final Office Action dated Mar. 25, 2019 in JP Application No. 2016-501927.

IMPI; Office Action dated Apr. 9, 2019 in MX Application No. MX/a/2015/012513.
IPONZ; Office Action dated May 10, 2019 in NZ Application No. 743173.
IMPI; Notice of Allowance dated May 27, 2019 in MX Application No. MX/a/2015/012513.
SIPO; Notice on Grant of Patent Right for Invention dated Jul. 8, 2019 in CN App. No. 201480026887.
WIPO; Written Opinion and International Search Report dated Jul. 11, 2019 in Int'l. Appl. No. PCT/US2018/048008.
IPAU; Examination Report dated Jul. 24, 2019 in AU Application No. 2018204275.
INPI; Preliminary Office Action dated Jul. 30, 2019 in BR Application No. 1120150227490.
IPAU; Examination Report dated Aug. 20, 2019 in AU Application No. 2016250989.
USPTO; Office Action dated Oct. 25, 2019 in U.S. Appl. No. 15/567,594.
EPO; Examination Report dated Nov. 7, 2019 in EP Application No. 14724546.8.
CIPO; Office Action dated Nov. 8, 2019 in CA Application No. 2,903,503.
JPO; Office Action dated Dec. 3, 2019 in JP Application No. 2016-501927.
IPONZ; Examination Report dated Dec. 23, 2019 in NZ Application No. 743173.
EPO; Examination Report dated Jan. 2, 2020 in EP Application No. 16725955.5.
IPIN; Examination Report dated Jan. 6, 2020 in IN Application No. 9132/DELNP/2015.
USPTO; Final Office Action dated Apr. 21, 2020 in U.S. Appl. No. 15/567,594.
Engineering Archives: Absolute, Gage, Vacuum and Atmospheric Pressures; pp. 1 and 2.
Vasquez-Caicedo et al., "High Pressure Stabilization of Wines: Impact of Pressure Change Technology on Wine Quality," Fraunhofer IGB (fraunhofer.eu), 1 page.

* cited by examiner

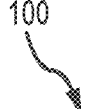
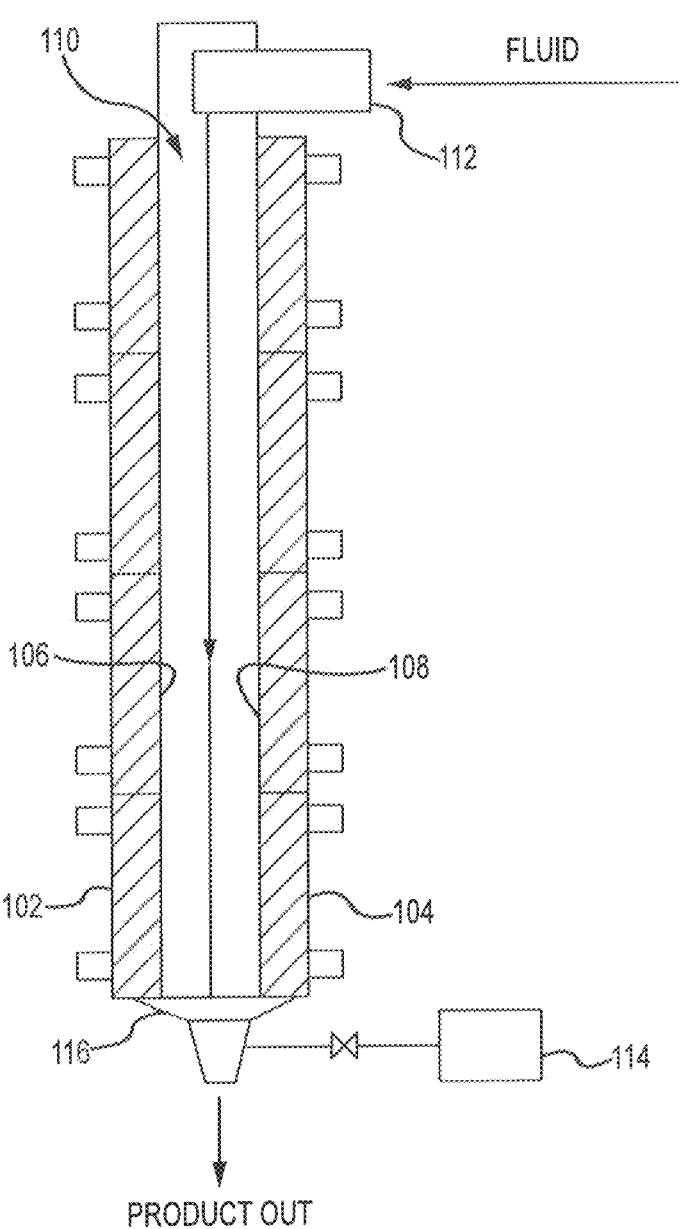
FIG.6

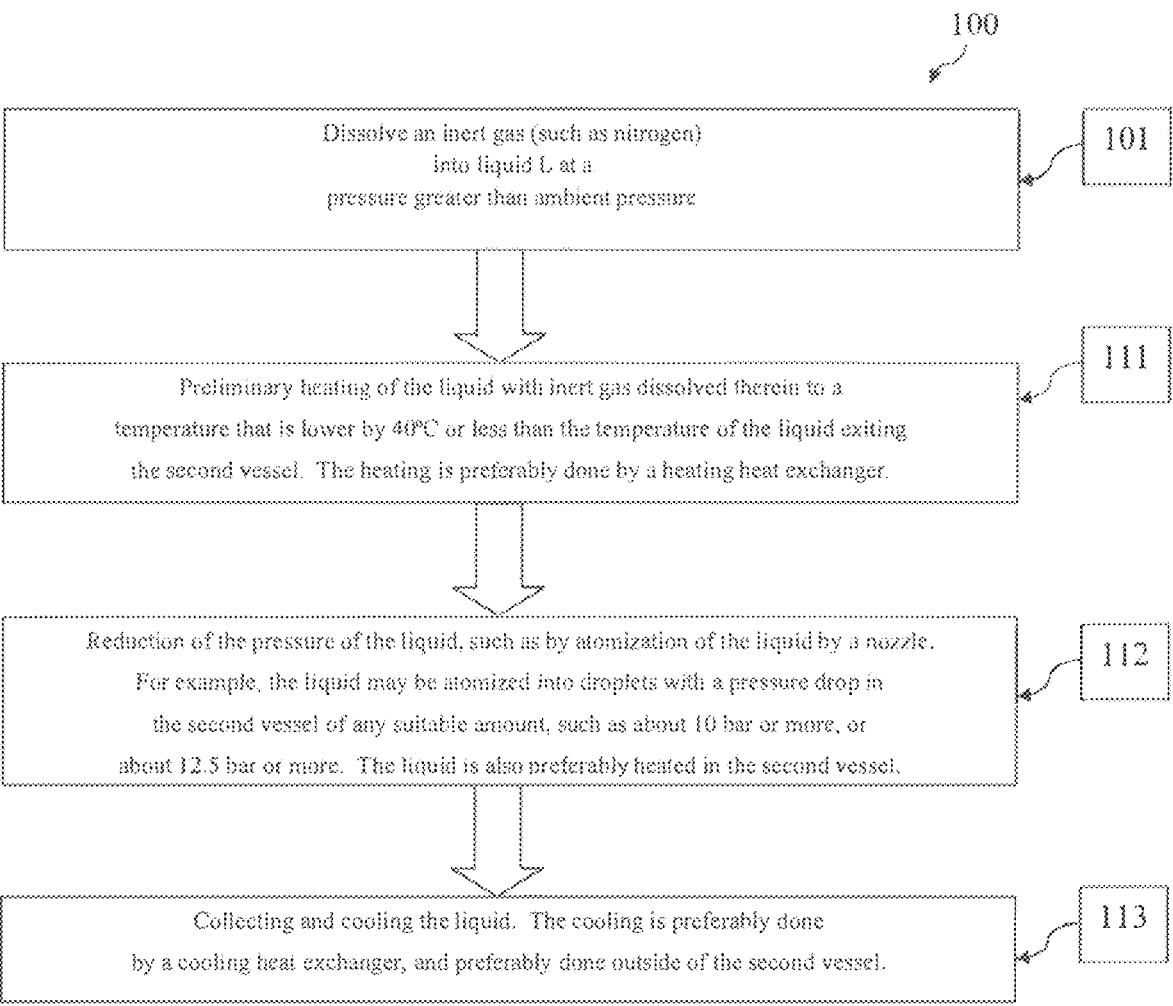

General Process Steps for One Exemplary Embodiment

100

| | |
|---|---|
| Dissolve an inert gas (such as nitrogen) into liquid L at a pressure greater than ambient pressure | 101 |

| | |
|---|---|
| Preliminary heating of the liquid with inert gas dissolved therein to a temperature that is lower by 40°C or less than the temperature of the liquid exiting the second vessel. The heating is preferably done by a heating heat exchanger. | 111 |

| | |
|---|---|
| Reduction of the pressure of the liquid, such as by atomization of the liquid by a nozzle. For example, the liquid may be atomized into droplets with a pressure drop in the second vessel of any suitable amount, such as about 10 bar or more, or about 12.5 bar or more. The liquid is also preferably heated in the second vessel. | 112 |

| | |
|---|---|
| Collecting and cooling the liquid. The cooling is preferably done by a cooling heat exchanger, and preferably done outside of the second vessel. | 113 |

Fig. 9

DEVICE AND METHOD FOR TREATING LIQUID

CROSS-REFERENCE TO RELATED APPLICATIONS

This application is a continuation-in-part of and claims priority to U.S. patent application Ser. No. 15/567,594 filed Oct. 18, 2017 entitled "Killing Microbes With Pressure Drop and Heat," which is a U.S. National Stage Application of PCT/US2016/029045 filed Apr. 22, 2016, which claims priority to, and the benefit of U.S. Provisional Patent Application Ser. No. 62/152,689 filed on Apr. 24, 2015 and U.S. Provisional Patent Application No. 62/209,039 filed on Aug. 24, 2015. This application is also a continuation-in-part of U.S. patent application Ser. No. 17/263,861 filed Jan. 27, 2021 entitled "Device and Method for Deactivating Pathogens in Blood Plasma, Blood Product and Biological Product" which is a U.S. National Stage application of PCT/US2018/048008 filed Aug. 24, 2018 and which claims priority to, and the benefit of, Russia Application Serial No. 2018127700, filed on Jul. 27, 2018. The disclosure of each of these applications that does not conflict with this application is incorporated herein by reference.

The following are also incorporated herein by reference to the extent they do not conflict with this application: RU 2277834, A23L 3/16, 20 Jun. 2006, PCT/US16/29045, 22 Apr. 2016, U.S. Pat. Nos. 7,708,941, 8,449,820, U.S. Patent Publication No. 2014/0261017, and U.S. Patent Publication No. 2018/0092385; U.S. Pat. No. 8,449,820, U.S. Publication No. 2014/0261017, U.S. Provisional Application No. 62/152,689, and U.S. Provisional Application No. 62/209,039.

FIELD

This disclosure includes methods and devices that utilize one or more of pressure, pressure drop, rate of pressure drop, temperature, rate of temperature increase, and inert gas, to kill and/or deactivate microbes (including pathogens) in a liquid. The system and method can be used for liquid products (referred to herein sometimes as just "liquid") in any industry, such as the food, vaccine or pharmacological industries. Some typical liquid food products are water, milk, other dairy products, fruit juice (such as orange juice), coconut milk, coconut water, coconut cream, beer, wine, a blood product, blood plasma, a biological product, coconut milk, a liquid food product, a pharmaceutical, a biological product, precursors for making a pharmaceutical, albumin, immunoglobulin, bovine colostrum, serums, culture media, vegetable juice, brewer's wort, wine base, or any liquid. All such liquids, plus any other liquid in which the number of microbes (including pathogens) are to be reduced, are collectively referred to herein as "liquid."

As used herein, "reduce" or "reducing" the number of microbes (including pathogens) means to kill and/or deactivate them. When deactivated, microbes (including pathogens) lose the ability to live and multiply normally, although they may still be alive.

BACKGROUND

There are known methods of thermal treatment of liquid intended to destroy or decrease the amount of microbes (including pathogens) in the liquid. In some known methods, the microbes are killed by heating the liquid, sometimes by mixing the liquid with a heating medium (e.g., steam) and maintaining the liquid at a temperature to pasteurize or sterilize the liquid.

One drawback of these known methods is that the liquid is mixed with excess water when the steam condenses. As a result water removal is necessary, which generally requires additional equipment, processing steps, time and expense. Another drawback of these known methods is potential deterioration of quality and taste after heating, regardless of how the heating is performed.

Another known method is one in which liquid is mixed with a heating medium of at a rate of about 1400° C./sec or more for pasteurization and about 7600° C./sec or more for sterilization to a temperature not exceeding the temperature at which qualitative changes in the liquid takes place (such qualitative changes and temperatures being known to those skilled in the art). The product is diffused into droplets preferably not exceeding 0.3 mm in diameter (this process is described in Russian Patent No. 2,052,967, the disclosure of which that is not inconsistent with the disclosure herein, is incorporated by reference). This method promotes efficient thermal treatment of the liquid, kills microbes (including pathogens) and its impact to the qualitative aspects of the liquid is less adverse, because it increases the rate at which the liquid product is heated and only maintains the product at a high temperature for a short duration. This method can be performed in a pasteurization device, which typically contains a liquid product diffuser, a pasteurization chamber, a nozzle for steam, a steam generator, a cooling chamber, and a vacuum pump.

A drawback of this method is that it still mixes the liquid with steam or hot air, which can adversely impact the stability of organoleptic and physicochemical properties (such as taste, odor, color, or consistency) of the liquid, and does not guarantee the necessary destruction of microbes (including pathogens) that are heat resistant.

SUMMARY

Methods and devices according to this disclosure are more likely to preserve much of the desirable baseline properties of the liquid, for example: the composition and biological activity of blood plasma proteins, or the liquid's color, taste, or nutritional value. This is due to the nature of one or more method steps, and the relatively short time in which some method steps are performed. In some embodiments, one or more method steps take place over a short period of time, such as in fractions of a second. Further, steam need not be used in some embodiments.

In accordance with various embodiments of the invention, a device is provided that includes a reactor. The reactor has an inner cavity and one or more nozzles that communicate with the inner cavity to diffuse droplets of liquid into the inner cavity. A reactor according to the invention may include any suitable inner cavity configuration and any number of nozzles positioned at any suitable locations on the reactor, wherein the nozzles each have an outlet that extends into the reactor to diffuse liquid product therein. The nozzles may be configured to reduce or eliminate an overlap of the droplets exiting the respective nozzles, and the reactor may have separate compartments, wherein one or more nozzles communicate with each compartment. Depending on the flow rate of liquid product through the reactor, one or more nozzles may be operated at one time.

The device may include a pump for increasing the pressure at the nozzle inlet, and a separate pump for regulating the pressure in the inner cavity. The device may include a first heat exchanger to heat the liquid before it enters the nozzle, and/or a second heat exchanger, which may be positioned inside and/or outside of the inner cavity, to heat the volume of liquid collected, and a pump to pump the liquid out of the reactor and most preferably past the heat exchanger. Further, the device may include a heater to heat the inner cavity of the reactor, or other structures to introduce one or more substances to heat the droplets exiting the nozzle.

This disclosure includes a liquid pressure and temperature treatment method and device that kills and/or mitigates the growth of microbes (including pathogens). One aspect of the invention is to subject the liquid to a pressure drop of five Bars or more or eight Bars or more, preferably as it passes through a nozzle where it is diffused into droplets that are sprayed into the inner cavity of a reactor (as used herein, one Bar equals 100,000 Pascals). Therefore, in one preferred embodiment, the pressure of the liquid at the nozzle inlet, which is where liquid enters the nozzle, is about five Bars greater or about eight Bars greater than the pressure at the nozzle outlet where the liquid exits as droplets into the inner cavity of a reactor. As used herein, eight Bars means approximately eight Bars and could be as low as 7.6 Bars, and may depend upon the amount the liquid product is heated after the pressure drop. Unless specified otherwise hereinafter in this application, however, eight Bars means 8.0 Bars. In accordance with aspects of the invention, the speed of the pressure drop of the liquid could be about $10^2$ Pa/sec or more, $10^3$ Pa/sec or more, $10^5$ Pa/sec or more, about $10^5$ Pa/sec to $10^{10}$ Pa/sec, about $10^9$ Pa/sec or more, eight Bars per millisecond or more, eight Bars per $\frac{1}{100}$ second or more, eight Bars per $\frac{1}{10}$ second or more, eight Bars per second or more, eight Bars per two seconds or more, eight Bars per five seconds or more, or eight Bars per ten seconds or more.

In accordance with further aspects, the process preferably includes diffusing the liquid into droplets (the droplets preferably having an average of about 100-200 um, or 30-500 um in diameter) during the pressure drop, although any suitable size or shape of droplets may be formed and the droplets need not be of uniform shape or size. The speed of the droplets exiting the nozzle may be about 5-10 m/sec or more. In other aspects, if multiple nozzles are used, the nozzles may be positioned to minimize or eliminate the overlap of droplets exiting different nozzles.

The liquid may be heated prior to entering the nozzle. The liquid is also preferably heated after, or while, being subjected to the pressure drop so that the temperature of the liquid is preferably increased by about 2.8° C. to 10° C. above the temperature of the liquid entering the nozzle. As used herein, heating a liquid means that all of the liquid is heated to at least the specified temperature in order to heat the microbes in the liquid to that temperature; and some or all of the liquid could be heated to a temperature higher than the specified temperature.

After the pressure drop, the liquid temperature is preferably increased by 2.8° C. to 10° C. to any suitable temperature, such as a temperature of between about 48° C. and 82° C., or between about 50° C.-75° C., or between about 62° C.-65° C., or up to 70° C., or up to 75° C., depending on the product being treated. Such temperatures are most preferably below the heat required for high temperature, short term ("HTST") pasteurization of the given liquid product. Further, the rate of heating the liquid product may be 1100° C./sec, or any amount from 1° C.-5° C., or between one second to sixty seconds per 1° C., or about 0.5° C. per second or less, about 1° C. per second, about 1° C. per ten seconds, or any amount from 1° C. per second and 10° C. per sixty seconds, but any suitable rate of heating can be utilized. The liquid may be heated using any known device or method. In one embodiment, the heating occurs without introducing steam, hot air, or any other substance into the liquid. Further, the heating is performed while the liquid is in droplets and/or after the liquid droplets have been collected into a liquid volume in a reservoir in the inner cavity of the reactor or at the outlet of the reactor. Heating the volume of collected liquid can occur inside and/or outside of the inner cavity of the reactor, preferably using any suitable heat exchanger, such as one of a type known to those skilled in the art.

In another embodiment, the liquid droplets are heated in the inner cavity (due to the temperature maintained in the inner cavity), or by introducing stream, hot air, or another substance while the liquid is in droplet form or after being collected into a liquid volume. In another embodiment, the liquid is partially heated in any desired manner while in droplet form and further heated in any desired manner after being collected into a liquid volume. For example, the liquid product may be heated by 2.8° C. or more while in droplet form and by another 2.8° C. or more after it has been collected into a liquid volume. Alternatively, the liquid may be completely heated in any suitable manner to the desired temperature while in droplet form. Regardless of how the temperature is raised by 2.8° C. or more, the liquid can be maintained at that temperature for any desired time, and by any suitable method, either while in droplet form and/or after being collected into a liquid volume.

The liquid product may be maintained at the 2.8° C. or higher temperature for any suitable period, such as at least 0.5 seconds, at least one second, at least two seconds, at least five seconds, at least ten seconds, at least twenty seconds, at least thirty seconds, at least one minute, at least two minutes, at least five minutes, at least ten minutes, at least twenty minutes, at least thirty minutes, or any amount of time from 0.5 sec to 30 minutes.

Another method according to this disclosure utilizes insert gas. As used herein, "inert" refers to a gas that does not significantly react with the liquid with which the gas is used, such that it would have a commercially negative effect on the liquid's properties. Some gases may be considered to be inert with respect to one liquid, but not with respect to another. One inert gas that may be used in embodiments of this disclosure is nitrogen. If utilized, the inert gas is dissolved into the liquid. For example, the inert gas can be transferred from an external starting container (such as a cylinder of compressed nitrogen), and delivered to a first vessel that contains the liquid. In the first vessel, at a pressure greater than ambient pressure, and in some preferred embodiments, about 5 Bars or more, about 10 Bars (in this description, one bar is equal to 0.1 MPa) or more, 6 Bars or more, 7 Bars or more, 8 Bars or more, 9 Bars or more, 12.5 Bars or more, or 13.5 Bars greater than ambient pressure, some of the gas is dissolved in the liquid. Ambient pressure is preferably about 1 Bar, but can be any suitable pressure. The greater pressure increases the amount of inert gas in the liquid (as measured in weight at atmospheric pressure and 21° C.), as compared to the amount of inert gas that would be in the liquid at ambient pressure inside of first vessel 70 after inert gas is introduced.

The pressure of the liquid and inert gas mixture is then reduced, such as by the liquid being released through a nozzle, so inert gas is released from the liquid. This physically damages and reduces the number of microbes (including pathogens) in the liquid. In exemplary embodiments, the pressure drops from about 5 Bars or more, or about 8 Bars or more, or any amount that does not exceed 10,000 Bars.

The liquid may also be heated before and/or after being pressurized in the first vessel, and/or when the liquid is in the second vessel. Other methods and devices are also disclosed, some of which do not use inert gas.

Any of the methods described above could be performed with different operating parameters. For example, the total pressure drop could be 5 Bars or more, the total amount of temperature increase of the liquid could be 2.8° C. or more, the temperature of the liquid after its temperature is increased by 2.8° C. or more could be any amount from 35° C. to 85° C., the average velocity of liquid droplets in the reactor can be any amount from about 5 m/sec or more, 7.6 m/sec to about 14 m/sec, or about 10 m/sec or more, or about 9.1 m/sec, the dwell time of liquid droplets in the reactor after leaving the nozzle and contacting a surface of the reactor or of a liquid volume could be any amount from 0.1 to 1.0 seconds, or about 0.4 seconds, and the average droplet diameter could be about 30-100 microns, or about 30-500 microns, and/or the total pressure drop can be from a high pressure of any amount from about 5 Bars or more to a lower pressure of about ½ to 1 Bar, or to a lower pressure of the liquid that is above the steam table pressure based upon the temperature inside of the reactor.

BRIEF DESCRIPTION OF THE DRAWING FIGURES

Exemplary embodiments of the present invention will be described in connection with the appended drawing figures, in which:

FIG. 6 illustrates a reactor in accordance with alternate aspects of the invention.

FIG. 9 illustrates a method of treating a liquid in accordance with an exemplary embodiment of the invention.

DETAILED DESCRIPTION

Figure 1:
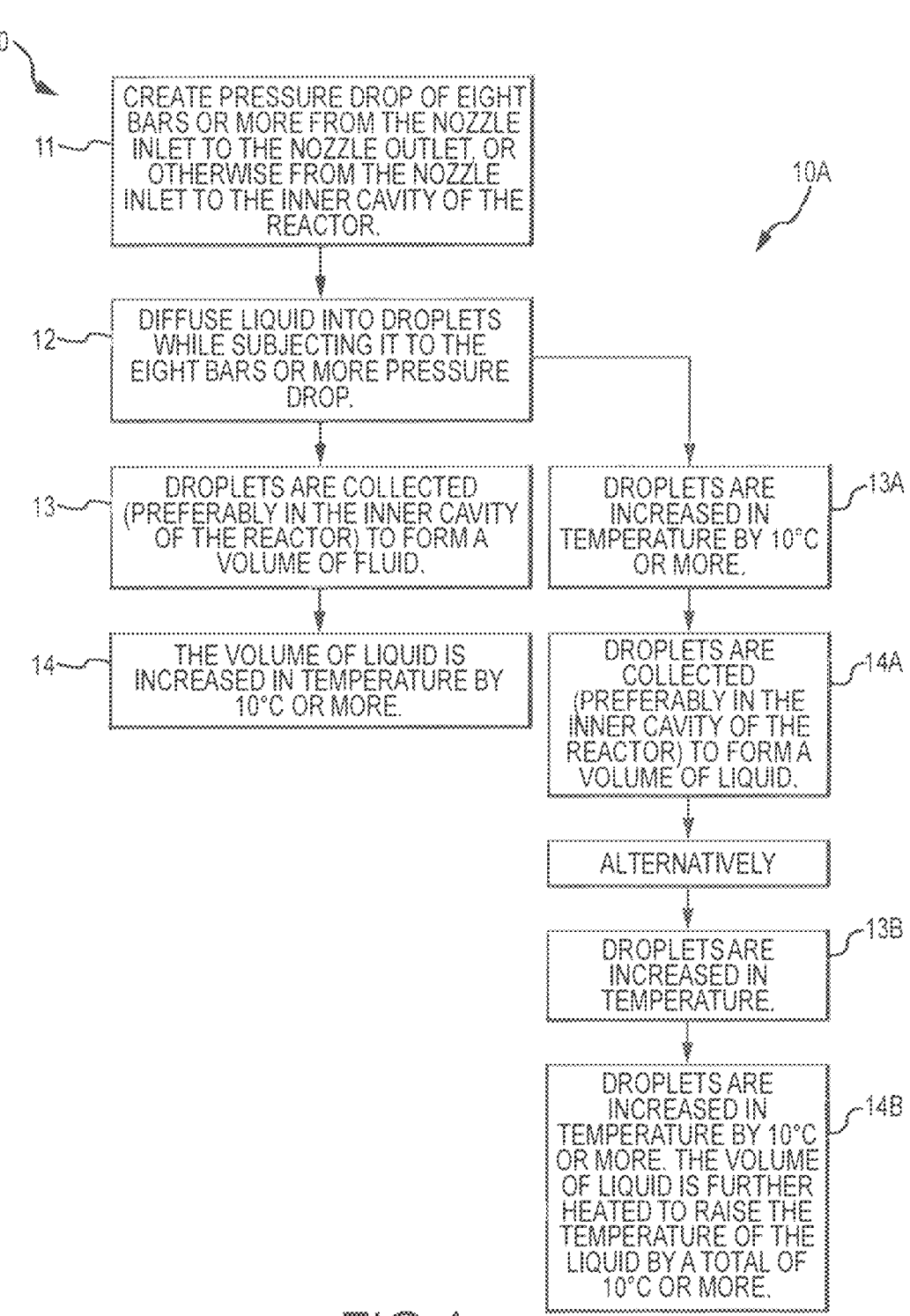
FIG. 1 illustrates a method of treating a liquid in accordance with embodiments of the invention.

FIG. 1 illustrates preferred methods 10 of treating a liquid in accordance with embodiments of the invention. Method 10 includes the steps of creating a pressure drop of about five Bars or more or about eight Bars or more. The pressure drop may occur from a nozzle inlet to the nozzle outlet when the liquid is diffused into droplets, wherein the nozzle outlet is preferably positioned in the inner cavity of a reactor (steps 11-12). Alternatively, a pressure drop of five Bars or more or eight Bars or more could occur as the liquid is diffused into droplets. The pressure variation is sufficient to destroy or weaken the outer membranes of microbes (including pathogens) or reduce the number of microbes (including pathogens) in the liquid. The pressure variation rate may be any suitable amount necessary to reduce the amount of, or weaken the membranes of the microbes (including pathogens) to be killed, and may be about $10^2$ Pa/sec or more, about $10^3$ Pa/sec or more, about $10^4$ Pa/sec or more, about $10^5$ Pa/sec or more, about $10^9$ Pa/sec or more, any rate from about $10^5$ Pa/sec to about $10^{10}$ Pa/sec, about eight Bars per ¹/₁₀,₀₀₀ second or more, about eight Bars per millisecond or more, about eight Bars per ¹/₁₀₀ second or more, eight Bars per ¹/₁₀ second or more, about eight Bars per second or more, about eight Bars per two seconds or more, about eight Bars per five seconds or more, or about eight Bars per ten seconds or more.

The preferred speed of the droplets exiting the nozzle is 5 m/sec or greater. The liquid may be diffused into droplets having an average diameter of about 100 microns to 200 microns or 100 microns to 400 microns, or 30 microns to 500 microns, but any suitable size or shape of droplets is sufficient, and the droplets may not be of the same size or shape.

Although not illustrated, method 10 may also include creating (1) a pressure at the inlet of a nozzle through which the liquid is diffused into droplets, and (2) regulating the pressure in the inner cavity of the reactor, wherein regulating the pressure may involve creating a vacuum or partial vacuum to assist in creating the eight Bars pressure drop. Method 10 also preferably includes a step (not shown) of heating the liquid before it reaches the nozzle inlet.

The liquid may enter the nozzle inlet at about 30° C. to about 90° C., or about 50° C. to about 70° C., or about 52° C. to 56° C., or up to about 75° C., or up to about 60° C., or up to about 65° C., or up to about 70° C., although prior to entering the inlet the liquid may be heated to any suitable temperature depending upon the liquid product type. The liquid is preferably heated by a first heat exchanger prior to the liquid entering the nozzle inlet.

While or after being subjected to the pressure drop, the liquid is diffused into droplets that preferably enter the inner cavity of the reactor, and may be heated while in the droplet phase. The liquid is preferably collected in the inner cavity of the reactor or at the outlet of the reactor to form a volume of liquid, also called a liquid volume (step 13). There is preferably one reservoir at the bottom of the reactor, but there could be more than one reservoir at more than one location in the reactor. The volume(s) of collected liquid may then be increased so the total increase in the liquid temperature is 2.8° C. or more as compared to the temperature at which the liquid enters the nozzle. The liquid volume, if heated, can be heated either in the reactor and/or outside of the reactor (step 14). The liquid temperature is properly raised using a second heat exchanger of any suitable type.

Alternatively, the liquid may be heated by 2.8° C. or more as it, or after it, exits the nozzle and is in droplet form. It may preferably be heated by the temperature maintained inside of the reactor chamber, or by interfacing the droplets with steam, hot air, or another substance. The liquid may also be partially heated as droplets and then fully heated to raise its temperature by 2.8° C. or more after being collected as the liquid in the reservoir. The liquid is maintained at the elevated temperature of 2.8° C. or more as compared to the liquid entering the nozzle for any suitable time, such as a period of at least 0.25 seconds, 0.1 to 1.0 seconds, at least 0.5 seconds, at least one second, at least two seconds, at least three seconds, at least five seconds, at least ten seconds, at least twenty seconds, at least thirty seconds, any amount from five seconds to thirty minutes, at least one minute, at least two minutes, at least five minutes, at least ten minutes, at least twenty minutes, or at least thirty minutes.

Method 10A has the same steps 11 and 12 as method 10. In step 13A, the liquid droplets are increased in temperature by 2.8° C. or more. The heating is preferably accomplished by subjecting the droplets to a suitable temperature inside of the inner cavity of the reactor, and not by mixing the droplets with steam or a hot air spray. In step 14A, the droplets are collected to form a volume of liquid. In steps 14A and 14B the liquid may be partially heated while in the droplet phase, for example by 2.8° C., and heated more, for example by another 2.8° C. after being collected as a liquid volume, so the total increase in the liquid temperature is 5.6° C. or more.

The temperature increase and rate of temperature increase can be of any rate suitable to kill selected microbes (including pathogens) in the specific liquid. For example, the rate of temperature increase may be 1100° C./sec, or any amount from 2° C./sec or more.

Device and Method Example 1

Figure 2:
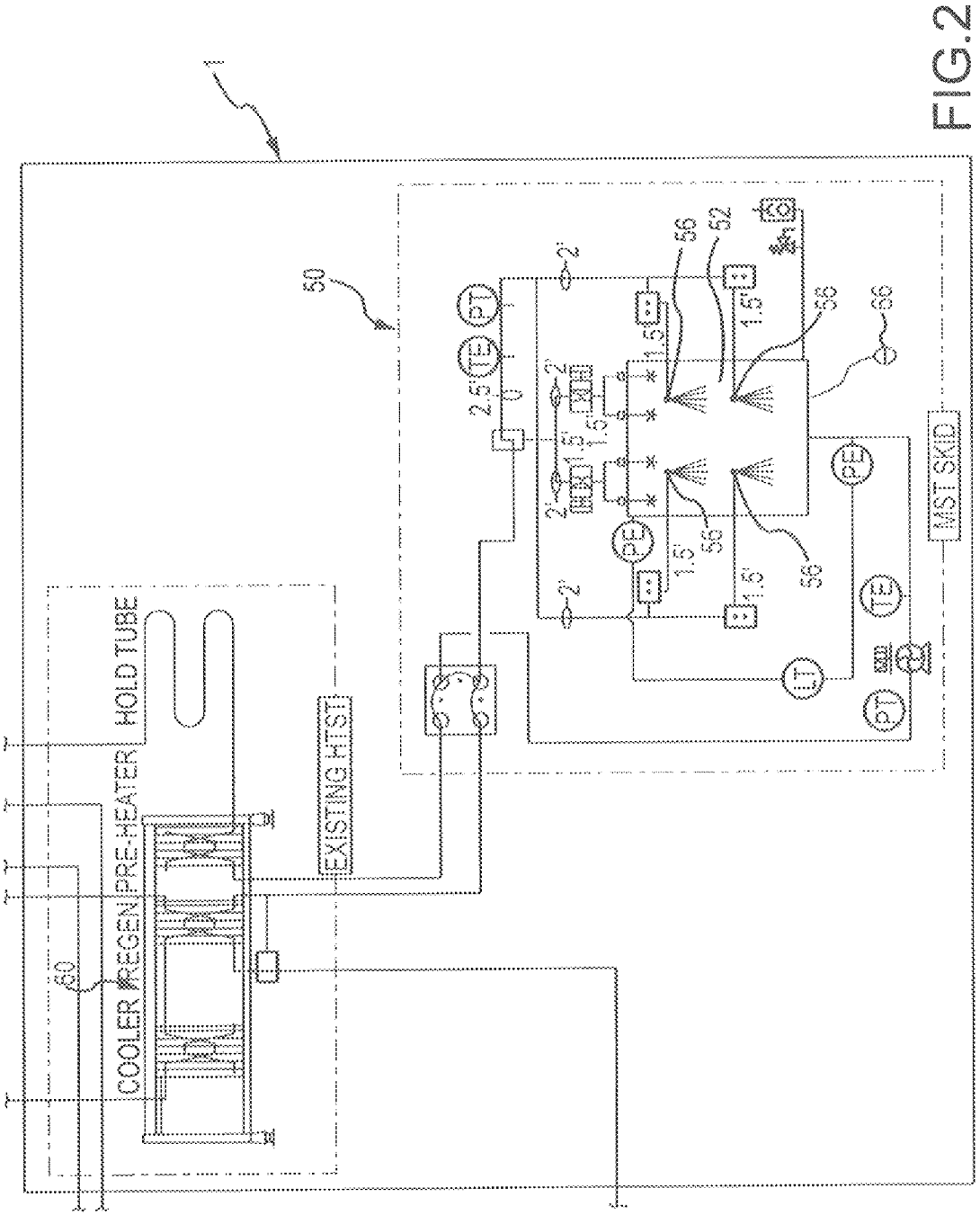
FIG. 2 illustrates a device for treating a liquid in accordance with exemplary embodiments of the disclosure.
Figure 3:
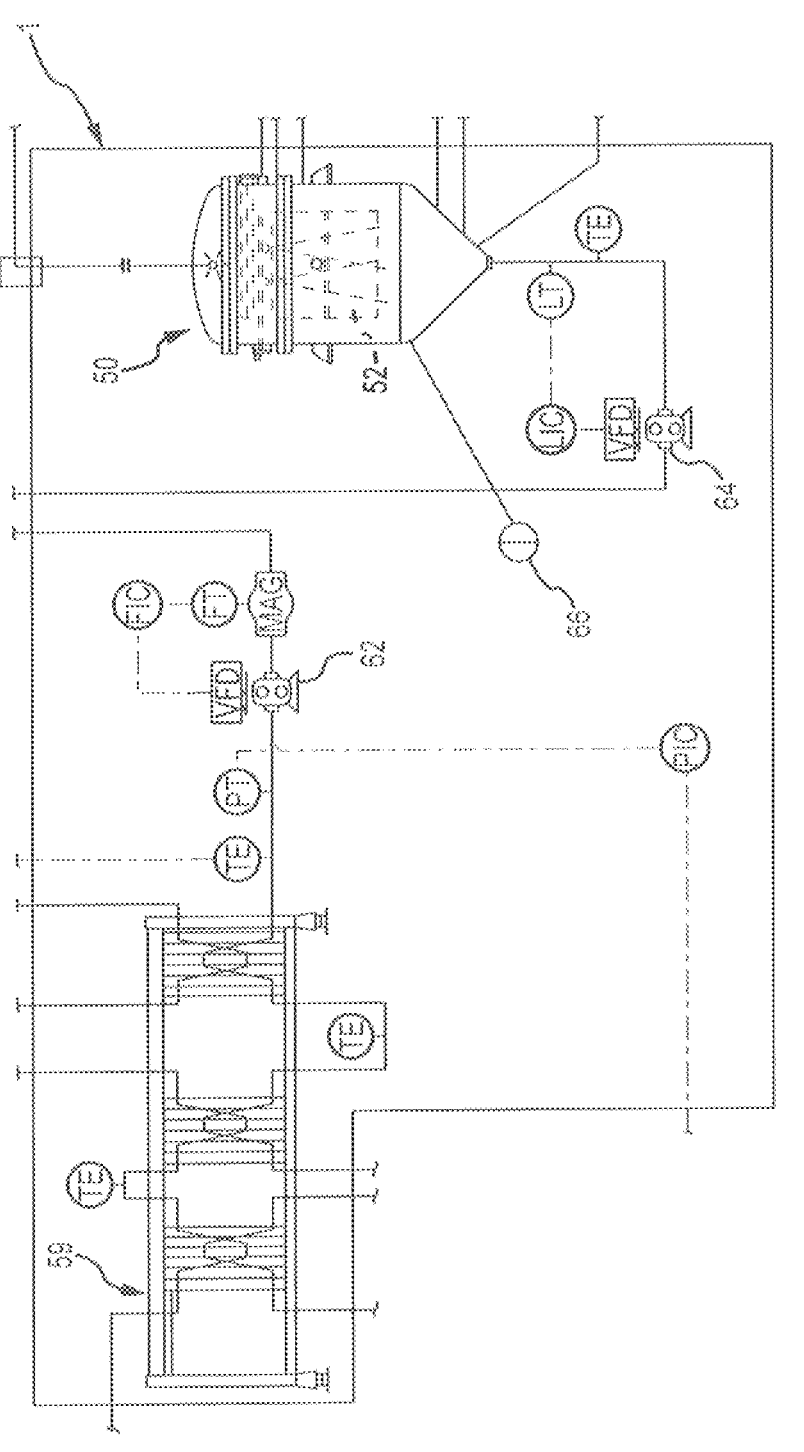
FIG. 3 illustrates other aspects of the device of FIG. 2.
Figures 4A, 4B, 4C:
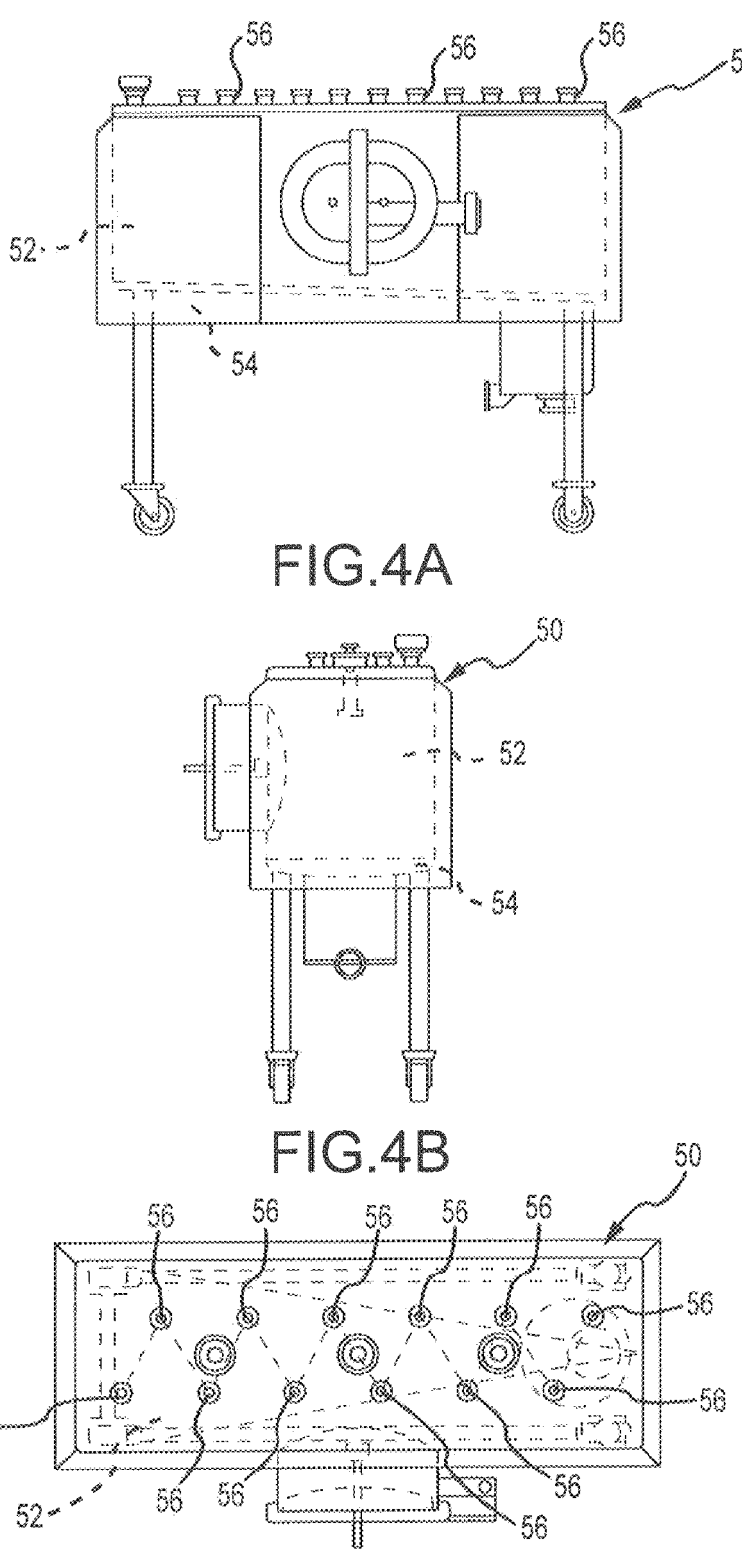
FIGS. 4A-4C illustrate a reactor illustrated for use in aspects of the invention.

Device 1, shown in FIGS. 2 and 3 can be used to practice methods according to the invention and, has a reactor 50 (best seen in FIGS. 4A-4C) according to the invention. Reactor 50 may have any suitable design, and any suitable design of inner cavity 52, such as being open (as shown in the Figures) or having separate compartments (not shown) that may or may not communicate with one another. In one embodiment, liquid droplets are formed by one or more nozzles 56, which are mounted on an outer wall of reactor 50 and have an outlet that extends into inner cavity 52, introduced into inner cavity 52, and eventually flow to reservoir 54 in inner cavity 52 (preferably at the bottom), and there is a sump 55 beneath the reservoir. The reactor 50 may be insulated by, for example, using one or more heating jackets (not shown) around the outside of reactor 50.

Figure 5:
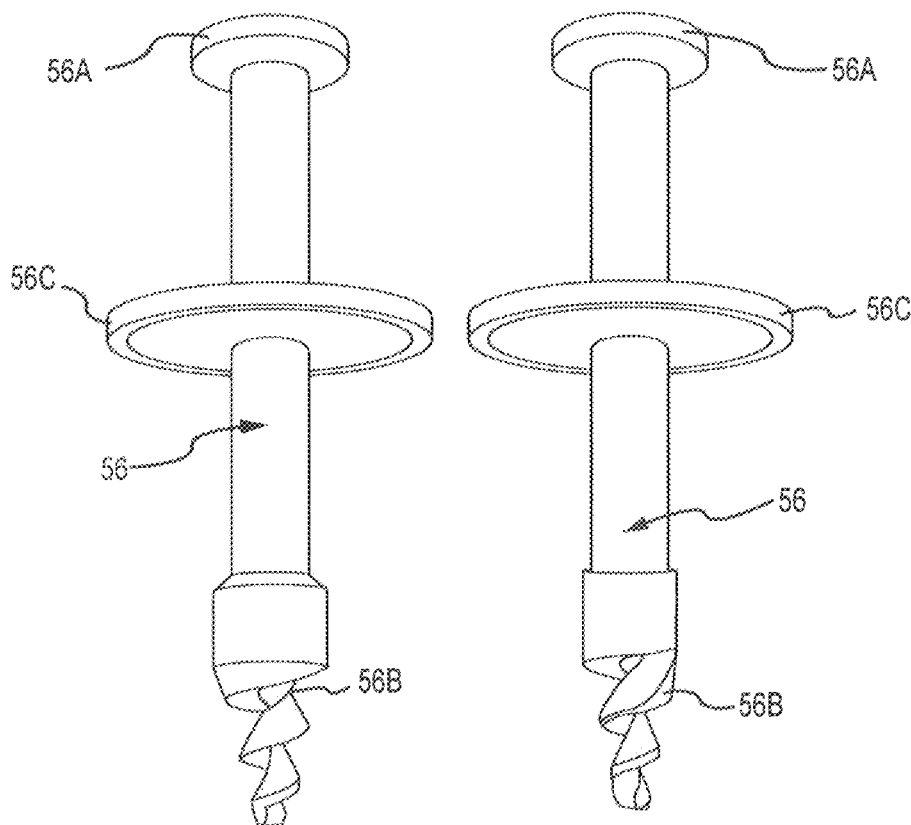
FIG. 5 illustrates a nozzle for use in treating a liquid in accordance with embodiments of the invention.

Reactor 50 includes at least one nozzle 56 (which is most preferably a stainless steel nozzle having any suitable nozzle, such as a nozzle having an inlet opening of 5 mm to 20 mm and an outlet opening of 3 mm to 20 mm in diameter, a preferred embodiment of which is best shown in FIG. 5). A preferred nozzle 56 preferably has an inlet 56A that is positioned outside of inner cavity 52 and an outlet 56B that is positioned inside of inner cavity 52. A brace 56C mounts in any suitable manner against an outer wall of reactor 50 to secure nozzle 56 to reactor 50. In the embodiment shown, there are twelve nozzles 56 positioned on reactor 50, with each nozzle diffusing approximately between one-half to two liters per minute, or up to ten liters per minute each, or up to 50 liters per hour each, or up to 200 liters per hour each, of liquid into inner cavity 52, although any suitable nozzle throughput may be used, and any size or type of nozzle to practice the invention may be used. Nozzles 56 are positioned such that there is little or no overlap in the spray coming from each nozzle entering the inner cavity 52. Any one or any combination of nozzles 56 may be operating at one time depending upon the type of liquid and the desired flow rate through reactor 50. Each nozzle also has an internal diffuser (not shown) that diffuses liquid entering the inlet 56A into droplets exiting the outlet 56B. Any suitable diffuser may be used, including those known in the art.

Device 1 further includes a heat source that preferably does not introduce a material, such as hot air or steam, into the liquid droplets entering the cavity 52 of reactor 50, although, as stated herein, hot air, steam or another substance may be mixed with the droplets to raise their temperature. A first heat exchanger 59 is preferably used to heat the liquid before it enters the inlet 56A of nozzle 56. Second heat exchanger 60 is provided that is of suitable width, length and temperature to heat by any desired amount the volume of liquid collected after diffusion, and preferably by 2.8° C. or more as described herein. As shown, heat exchanger 60 is entirely outside of reactor 50, but it could be entirely or partially inside of reactor 50. Device 1 may also have a pump 62 for pressuring the liquid entering the nozzle inlet 56A and a vacuum pump 64 for regulating the pressure of inner cavity 52. Further, a heater 66 may be used to increase the temperature in inner cavity 52.

In one aspect of a method according to the invention a liquid is sent under pressure to inlet 56A of nozzle 56 where it is diffused into droplets that enter inner cavity 52 through nozzle outlet 56B. Using milk as an example, the liquid enters nozzle 56 at preferably 52° C. to 56° C. (although any suitable temperature may be selected), and may be increased in temperature by 2.8° C. or more while being diffused as it exits the nozzle outlet 56B. The speed of the pressure drop for the liquid product is sufficient to kill or weaken the membranes of microbes (including pathogens) to be killed, and some preferred rates of pressure change are set forth herein.

The liquid droplets are collected into one or more volumes of liquid in reservoir 54 or at the reactor outlet after being diffused into the inner cavity 52 or at the outlet of the reactor. The volume(s) of liquid may then be increased by the total of 2.8° C. or more (and the liquid may have been increased in temperature while in the droplet phase), either inside and/or outside of the reactor, such as by second heat exchanger 60.

Device and Method Example 2

Device 2 functions the same as device 1 except that it includes a reactor 100 that has a different design than reactor 50. Device 2 can also be used to practice methods according to the invention, which have already been described. FIG. 6 illustrates device 2 with a reactor 100 in accordance with exemplary embodiments of the invention.

Reactor 100 utilizes the same methods to treat liquid as already described, but has a different configuration, and optionally a different nozzle design, than reactor 50. As shown, the walls, surfaces and inner cavity of reactor 100 are substantially vertically oriented, although they may be cylindrical or of any suitable configuration. Reactor 100 as shown includes two parallel walls 102, 104 and a nozzle 112. Each wall 102, 104 has an interior surface, 106, and 108, respectively. An interior space 110 between interior surfaces 106, 108 defines at least part of an inner cavity within reactor 100. The walls 102, 104 may be coupled together using any suitable technique, such as welding, or the walls may be integrally formed. By way of one example, walls 102, 104 may have dimensions of 1200 mm×1200 mm and the spacing between the walls may be about 60 mm. Walls 102, 104 may be formed of any suitable material, such as stainless steel and have any suitable dimension or space between them. Reactor 100 may include additional walls, not illustrated, to form an inner cavity 110 within the reactor. Reactor 100 includes a reservoir 116 to collect liquid. Optionally, it may also include a vacuum source 114, which is preferably a vacuum pump, to regulate the pressure inside of cavity 110.

During operation of reactor 100, pressurized liquid is introduced at an entrance of reactor 100, e.g., near or at the top of reactor 100, via nozzle 112, and the liquid is projected downward as a flat spray (in this embodiment) between the inner surfaces 106, 108, respectively of walls 102, 104. As used herein "flat stream" or "flat spray" means a spray that is substantially planer. By way of examples, the spray may be substantially planer in a first direction and an angle of the spray in a direction perpendicular to the first direction may be about twenty degrees or less, about ten degrees or less, about five degrees or less or about two degrees or less. The spray is preferably about 5 mm to 30 mm thick. Alternatively, nozzle 112 may release any shape of spray into inner cavity 110, which could be of any suitable configuration.

As the liquid passes through nozzle 112 and is diffused into droplets, it preferably undergoes a rapid change in pressure as described above, and the total drop in pressure could be about five Bars or more.

In the illustrated example, wall 102 and wall 104 are vertical and the liquid spray travels from an entrance downward towards the bottom of the reactor 100 and is collected in reservoir 116.

In another embodiment not illustrated, the walls may not be parallel, but may be in the shape of an inverted "V," with them being closest at the top where the flat liquid spray is introduced. Alternatively, they could be formed in a "V" shape with them being farthest apart at the top where the liquid spray is introduced.

Although reactor 100 is illustrated with two walls, a reactor in accordance with the present invention may have greater than two walls and a plurality of interior spaces; one space being between every two wall surfaces. Each interior space defined by two wall surfaces may have one or more nozzles at an entrance to the space, such that the droplets exiting the one or more nozzles are projected into the space.

Figure 8:
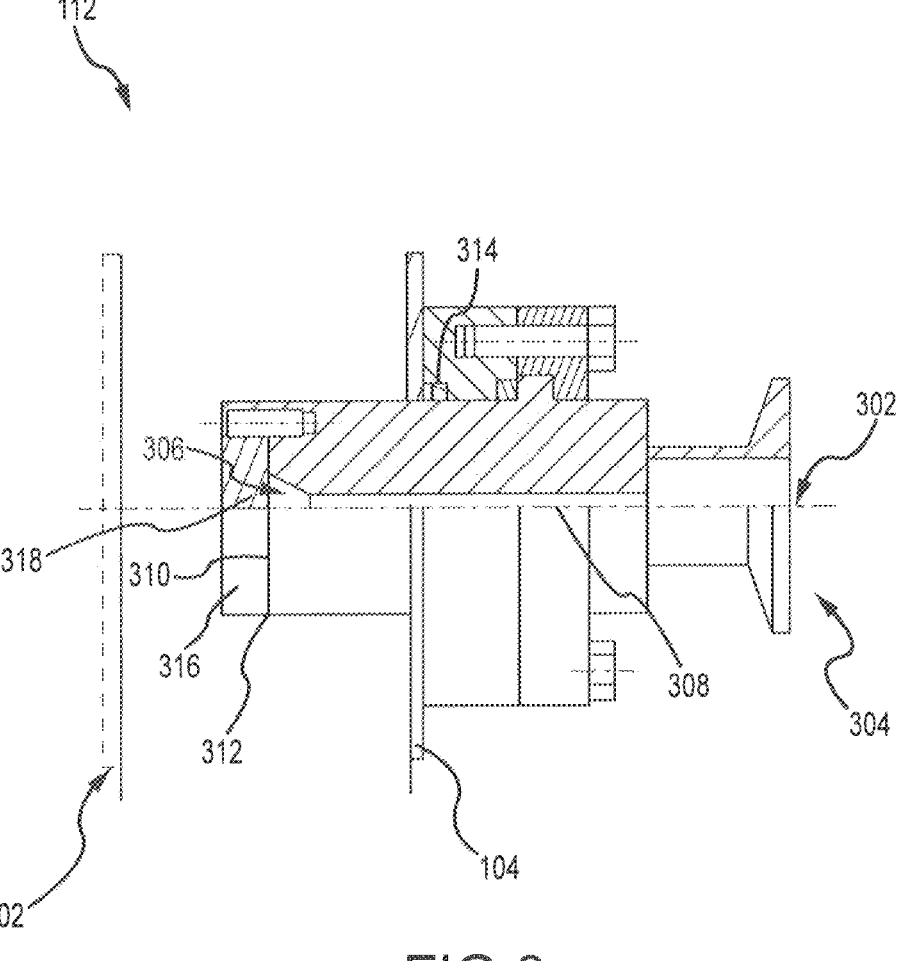
FIG. 8 is a view of an alternate nozzle that may be used in the practice of the invention.

Nozzle 112 is located at an entrance to inner cavity 110. An exemplary nozzle 112 converts an incoming stream of liquid (e.g., a cylindrical or conical stream) flowing in a first direction to a flat stream flowing in a second direction. In the illustrated example, the second direction is perpendicular to the first direction. FIG. 8 illustrates exemplary nozzle 112 in greater detail. Nozzle 112 includes an inlet 302 at a first end 304, a tapered end 306 at an end of a conduit 308 between first end 302 and tapered end 306. Inlet 302 and conduit 308 may have a diameter between about 1 and 3 mm. Nozzle 112 also includes an interior structure 310 that receives liquid from conduit 308 or tapered end 306 (e.g., in a cylindrical or conical pattern) and converts the liquid to a flat spray pattern, as illustrated in FIG. 2, which exits at end 312 of interior structure 310. The thickness of the flat spray exiting the nozzle may be no more than 5 mm, no more than 10 mm, no more than 20 mm, or no more than 30 mm. Alternatively, any suitable nozzle may be used with this reactor design, such as previously described nozzle 56.

Interior structure 310 may include, for example, a flat plate, which may be in the shape of a disc. Interior structure 310 includes a leading edge 318 distal to end 312. The volume of the liquid exiting nozzle 112 may be, for example between about 500 Uhr (liters per hour) to 1000 Uhr or more. Nozzle 112 may be formed of any suitable material, such as food-grade stainless steel.

Figure 7:
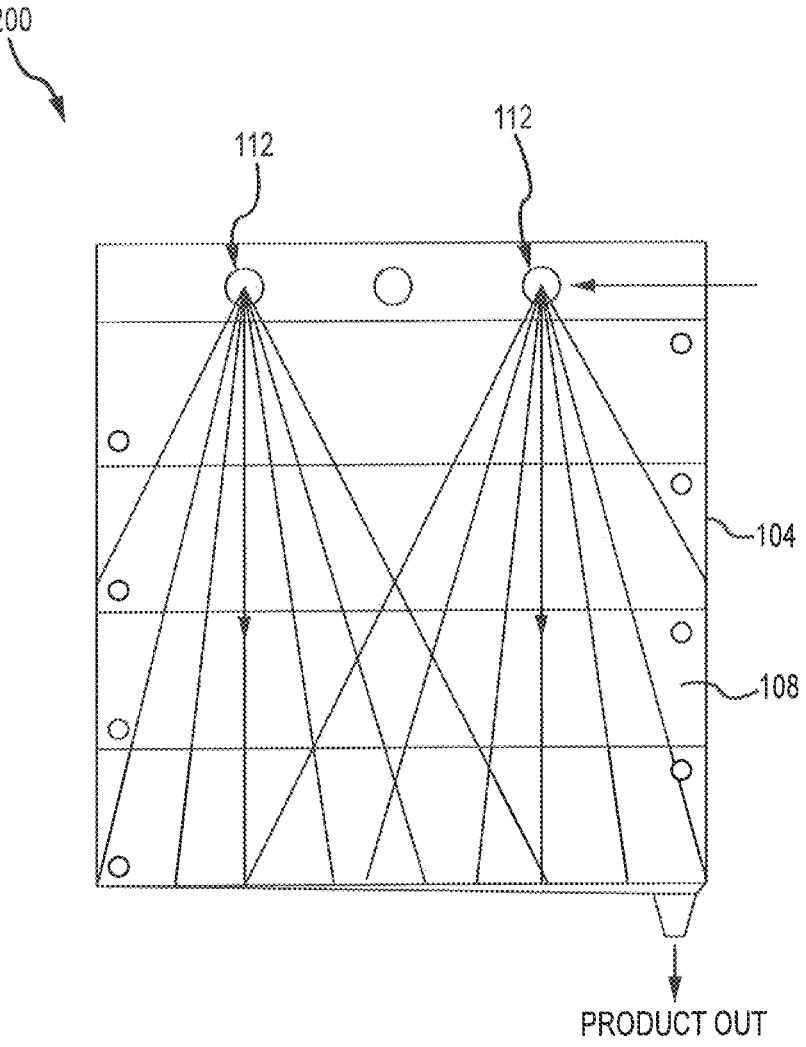
FIG. 7 is an alternate view of the reactor of FIG. 6.

Nozzle 112 may be attached to one or more walls 102, 104 using any suitable technique. By way of example, nozzle 112 may include a gasket ring 314, a clamping disc 316, and a fastening mechanism, such as a screw 318 to secure nozzle 112 to wall 104. Nozzle 112 may be fastened such that spray from nozzle 112 is centered between the surfaces 106, 108, respectively, of walls 102 and 104, as illustrated in FIGS. 6-7.

In accordance with exemplary embodiments of the invention, nozzle 112 is designed to create droplets having a diameter generally not exceeding on average about 100-200 microns, or from 100 to 500 microns. A speed of the droplets in reactor may be any amount of about 5-10 m/sec or more, although this may vary according to desired operating parameters.

Optional vacuum source 114 may include any suitable vacuum pump. Vacuum source or pump 114 may be configured to maintain a pressure in inner cavity 110 of any suitable amount, and preferably any amount from about one Bar to about 0.25 Bar, or any amount from about ½ Bar to 1 Bar.

ALTERNATE EMBODIMENTS

Figure 10:
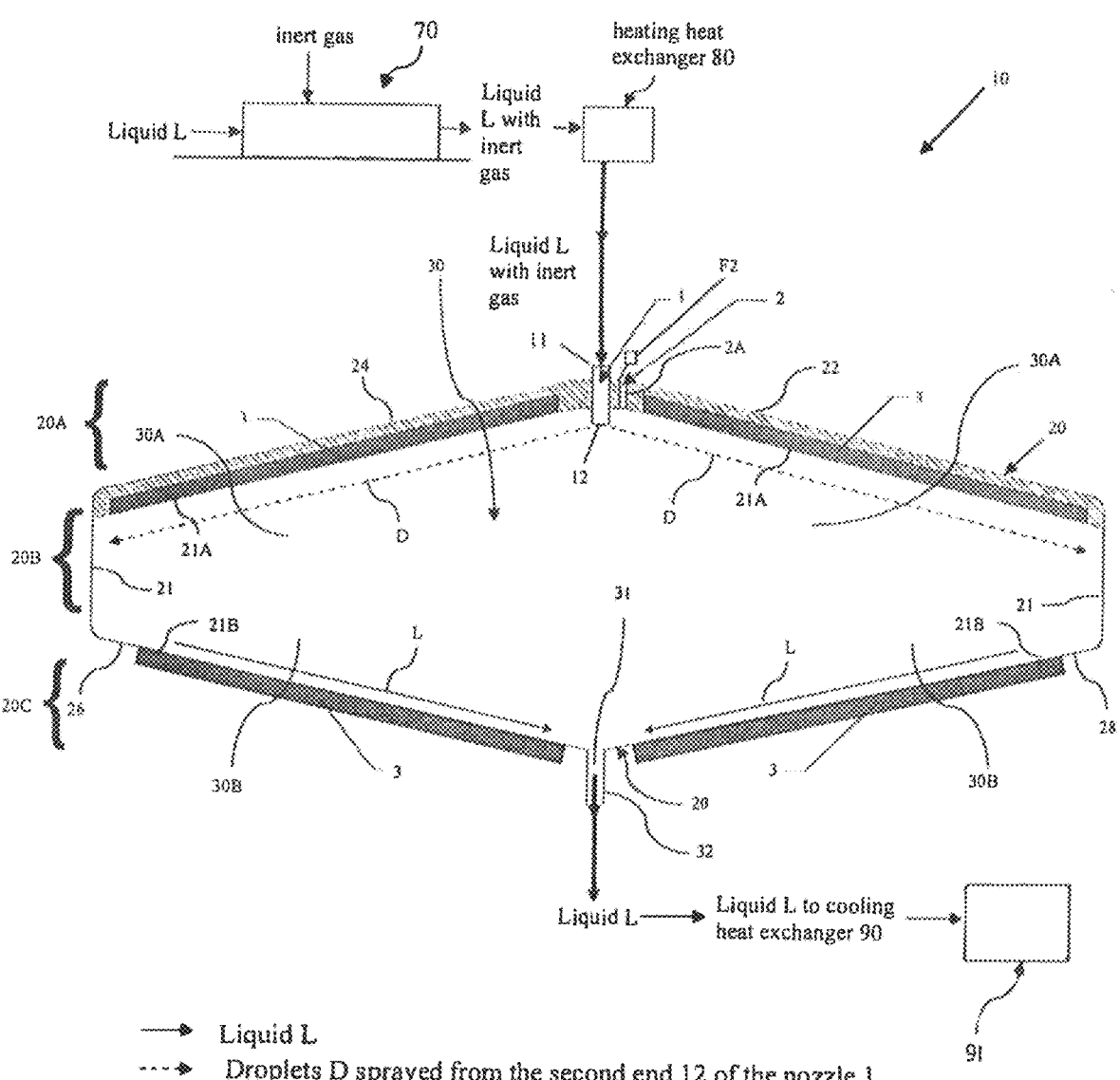
FIG. 10 illustrates a device for treating a liquid in accordance with an exemplary embodiment of the disclosure.

FIG. 9 illustrates general process steps for an alternate exemplary method 100, and FIG. 10 illustrates an exemplary device 10 that can be used to implement the method 100 or other methods.

Turning now to FIG. 10, a basic illustration of an exemplary device 10 to perform a method disclosed herein is shown. Device 10 includes first vessel 70, heating heat exchanger 80, second vessel 20, and cooling heat exchanger 90. Liquid L flows or is pumped into first vessel 70, and inert gas is dissolved into the liquid L. The liquid L entering first vessel 70 can have a temperature that is about 4° C. to 25° C., although any suitable temperature would suffice.

First vessel 70 can be of any suitable material, shape, size, or construction for inert gas to be dissolved into a liquid. First vessel 70 preferably is in fluid communication, such as by one or more pipes, with heating heat exchanger 80. Heating heat exchanger is preferably in fluid communication, such as by one or more pipes, with second vessel 20. Second vessel 20 has an exit 31 leading to an exit pipe 32 that leads outside of vessel 20. In this embodiment, the liquid exiting vessel 20 may be cooled in cooling heat exchanger 90.

Second vessel 20 can be of any suitable shape and size. In the embodiment shown, vessel 20 has an upper frustoconical portion 20A, a generally cylindrical center portion 20B, and a lower frustoconical portion 20C.

In step 101, the liquid L in first vessel 70 has an inert gas (such as nitrogen) dissolved into it. In one embodiment, liquid L is first introduced into the first vessel 70, preferably by being pumped into vessel 70. Prior to being introduced to first vessel 70, the pressure of the liquid may be lowered, such as to one Bar. The liquid L may also be cooled or heated before being introduced into first vessel 70. For example, the liquid L may be cooled or heated to the temperature of the room in which first vessel 70 is located.

Inert gas is added to the first vessel 70, preferably after the liquid L is in first vessel 70, at a pressure greater than ambient pressure, such as a pressure greater than ambient pressure by about 5-10 Bars, or any pressure greater than ambient pressure by: from about 10-15 Bars, about 13.5 Bars, about 12.5 Bars or more, about 2 Bars or more, about 3 Bars or more, about 4 Bars or more, about 5 Bars or more, about 6 Bars or more, about 7 Bars or more, about 8 Bars or more, about 9 Bars or more, about 10 Bars or more, about 11 Bars or more, about 12 Bars or more, about 15 Bars or more, or about 5 Bars to about 10 Bars, about 9 Bars to about 12 Bars, about 9 Bars to about 10.5 Bars, or about 9.5 Bars to about 13.5 Bars.

Inert gas is preferably introduced into the first vessel 70 at a higher pressure than the liquid L is maintained inside of first vessel 70 before the inert gas is added. For example, the liquid L may be at about 1 Bar inside of vessel 70 and the inert gas may be introduced at a higher pressure in order to raise the overall pressure inside of first vessel 70.

The first pressure is selected based on the type of liquid and the microbes (including pathogens) present in the liquid. In one example, the liquid is bovine colostrum and the first pressure is about 9 Bars or more. In another example, the liquid is human blood plasma and the first pressure is about 13.5 Bars or more. A pressure drop of 5 Bars or more would, however, be suitable.

The inert gas can be supplied from any suitable source, such as from an outside source (e.g., a cylinder of compressed nitrogen). When introduced into the first vessel 70, at least some of the introduced inert gas is dissolved in the liquid L. This increases the concentration of inert gas in the liquid L to a weight amount as measured at 1 Bar and 21° C. that is greater than the amount of inert gas that would be in the liquid L in first vessel 70 at ambient pressure (1 Bar) after the inert gas is introduced. For example, the amount of inert gas in the liquid L may be any amount by weight as measured at atmospheric pressure and at 21° C. from about 5% and about 1,000% greater than the weight amount of inert gas that would be in the liquid in first vessel 70 at 1 Bar pressure at 21° C. The amount of inert gas could be about 10% or greater, about 20% or greater, about 30% or greater, about 40% or greater, about 50% or greater, about 75% or greater, about 100% or greater, about 200% or greater, about 300% or greater, about 400% or greater, about 500% or greater, about 600% or greater, about 700% or greater, about 800% or greater, about 900% or greater, or about 1,000% or greater, or about 2,000% of greater, than the weight amount of inert gas that would be in the liquid L at 1 Bar and at 21° C. in first vessel 70 when inert gas has been introduced.

The liquid with inert gas dissolved into it at a pressure greater than 1 Bar may be referred to herein as a "mixture," or as a "liquid/gas mixture," but is usually referred to as "liquid" or "liquid L." Prior to having the inert gas dissolved into it at a pressure greater than 1 Bar, and after the pressure drop, "liquid" means the liquid L, which may or may not include some inert gas.

Referring to FIG. 9 and FIG. 10, in step 111 the liquid L with inert gas (and still under pressure) is preferably moved under pressure from first vessel 70 (which may be done using a pump) to a heat exchanger 80 and preferably heated. Alternatively, the liquid may be heated in vessel 70, and/or heated at any point between vessel 70 and nozzle 1, or not heated until it enters cavity 30 in vessel 20.

In step 111, the liquid with inert gas is preferably heated to any suitable temperature of about 40° C. to about 60° C., or about 40° C. to about 58° C., or about 35° C. to about 48° C., or about 35° C. to 85° C. The temperature of the liquid L after being heated in this step is preferably lower by about 40° or less, or 50° C. or less, or any temperature from about 10° C.-50° C. or less, than the temperature of the liquid L that exits (through exit 31) vessel 20. The temperature of the liquid L exiting exit 31 depends upon the type of the liquid, and the temperature is preferably less than the pasteurization temperature of the liquid, and may be about 35° C.-85° C. when it exits the second vessel 20. In one example the liquid is bovine colostrum that is heated to a temperature of about 40° C. to about 60° C. in the second vessel. In another example, the liquid is human blood plasma that is heated to a temperature of about 37° C. to about 48° C. in the second vessel.

In step 112, atomization of the liquid L, for example, into droplets of 30-500 μm diameter, with a pressure drop in the cavity 30 of second vessel 20 occurs. At this step the inert gas is released from liquid L. Alternatively, the pressure drop could be accomplished in any other suitable manner.

As shown in FIG. 10, the pressure drop is accomplished in this embodiment by passing the mixture into first end 11, and through nozzle 1, wherein the liquid is converted into a spray of droplets and inert gas is released from the liquid as it exits second end 12. The speed of the droplets may be about 5 m/sec or more, 7.6 m/sec to 14 m/sec, 9.1 m/sec, 40 m/sec, or 40 m/sec or more, or 10 m/sec or more. Or, the speed may be about 100 m/sec or less. The average droplet diameter is any suitable amount, and may be any dimension from about 30 micrometers to about 300 micrometers, or about 30 micrometers to 500 micrometers. For bovine colostrum, the average droplet diameter may be about 150 to about 300 micrometers. For human blood plasma, the average droplet diameter may be about 30 to about 150 micrometers.

The reduction in pressure causes inert gas to be released from the liquid L, which should reduce the number of microbes in liquid L. The reduction in pressure is calculated by subtracting the pressure in cavity 30 from the pressure of the liquid/inert gas mixture entering nozzle 1. For example, the total reduction in pressure may be 12.5 Bars (e.g., the pressure of the liquid/inert gas mixture entering first end 11 of nozzle 1 would be 13.5 Bars, and the pressure inside of cavity 30 would be 1 Bars). The pressure in cavity 30 may be greater than 1 Bars, such as any amount up to about 4 Bars, or it may be less than 1 Bars, or may be 5 Bars or more, about 2-15 Bars, or about 2 Bars or more, about 3 Bars or more, about 4 Bars or more, about 5 Bars or more, about 6 Bars or more, about 7 Bars or more, about 8 Bars or more, about 9 Bars or more, about 10 Bars or more, about 11 Bars or more, about 12 Bars or more, about 12.5 Bars or more, about 13 Bars or more, about 14 Bars or more, about 15 Bars or more, any amount from about 12 Bars-15 Bars, any amount from about 10 Bars-15 Bars, about 10-12.5 Bars.

The rate of reduction in pressure in cavity 30 can be any suitable amount, and may be at any rate between about 1 Bars/sec to about 10,000 Bars/sec, and preferably not greater than 10,000 Bars/sec, although it could be slower or faster, depending upon the type of equipment used, the type of liquid, and the type of microbes (including pathogens).

In the preferred device shown in FIG. 10, the nozzle 1 converts the liquid L into a spray of droplets falling onto a surface, such as internal surface 21 of the second vessel 20 into which the liquid L is sprayed, or the droplets may land on the bottom of the reactor. The droplets are preferably heated in cavity 30, such as by an external heating source (shown as heating jackets 3) with circulating hot water, or any other appropriate heating method outside or inside of second vessel 20.

The liquid L is preferably heated from a temperature of about 35° C. to 90° C. before it enters cavity 30 to about 35° C. to 85° C. inside of cavity 30. In one example, the liquid is bovine colostrum that is heated to about 55° C. to about 80° C. in second vessel 20. In another example, the liquid is human blood plasma that is heated to about 45° C. to about 60° C. in the second vessel. The preferred heating rate is of about 3,000° C./sec-5,000° C./sec, or 4,000° C./sec, or any amount from 2° C./sec or more, but may be any sufficient amount to further decrease the amount of microbes (including pathogens), such as about 500° C./sec or more, or any rate of about 500° C./sec to about 7,000° C./sec, or about $10^{2}$° C./sec-$10^{3}$° C./sec, about $10^{3}$° C./sec-$10^{4}$° C./sec, any rate from about 1,000° C./sec-2,000° C./sec, any rate from about 2,000° C./sec-3,000° C./sec, any rate from about 3,000° C./sec-5,000° C./sec, or any rate from about 5,000° C./sec-6,000° C./sec.

As the liquid is released through second end 12 of nozzle 1 and into cavity 30, the liquid L is preferably converted into a spray of droplets D. In one embodiment, droplets D do not touch the upper, inner wall 21A of top portion 20A. The droplets are projected outward at an angle and preferably first touch either inner wall 21 of portion 20B, or inner wall 21B of lower portion 20C. The droplets D collect and form a volume of liquid L that flows towards exit 31, where the liquid exits vessel 20 through pipe 32.

In step 113, the liquid is collected and preferably cooled to any suitable temperature, such as any temperature from about 8° C.-25° C. after it is collected in the second vessel 20. Such cooling, if performed, is preferably done by a cooling heat exchanger 90 that is outside of vessel 20, at a preferred rate of any amount from about 0.5° C.-5° C./sec. Any suitable cooling method and rate, however, may be used. For example, the cooling rate may be about 2° C./sec, about 3° C./sec, about 4° C./sec, about 5° C./sec, about 6° C./sec, any rate from 0.5° C./sec to 10° C./sec, or any rate from 0.25° C./sec to 1° C./sec. In one example, the liquid is human blood plasma that is cooled to about 8° C. or lower. In another example, the liquid is orange juice and the temperature is lowered to about 25° C. or lower. Then, the cooled liquid is collected in a finishing container, from which it can be sterilely removed.

The temperature to which a liquid is heated depends on the type of liquid and microbes (including pathogens). When the liquid and/or liquid/gas mixture is heated, the temperature to which it is heated should not be high enough to significantly diminish the desirable qualities of the liquid. Some liquids should not be heated to, or heated above, their pasteurization temperatures.

Second vessel 20 may be fitted with a valve 2 to equalize pressure (preferably automatically) with the ambient, external pressure, which is preferably about 1 bar. There is preferably a pipe 2A from the valve 2, wherein the pipe 2A runs to a filter F2 for purification of the air-gas mix that enters cavity 30 through valve 2. The filter reduces or eliminates microbes (including pathogens) from outside the second vessel 20 that might otherwise enter cavity 30.

While this disclosure is not limited to any particular theory of operation, the gas pressurized into the liquid L is forced out of the liquid droplets D because of the reduction in pressure in cavity 30. This is believed to help to kill microbes (including pathogens), which (based on experimentation) converge on the external surface of the liquid droplets. The inert gas molecules that exit the liquid are believed begin to combine in clusters forming numerous, larger bubbles. In some examples, these expand to hundreds of times the size in a fraction of a second. In localized areas of the droplets, the gas molecule clusters have been observed to cause microexplosions and bursting of bubbles. Numerous localized changes in pressure result in the mechanical destruction of bacteria cell membranes, viral envelopes, and interfere with their receptor functions. The process is rapid, and the microbes (including pathogens) are not able to adapt to the rapid changes in environment. The simultaneous heating of the liquid along with the pressure drop intensifies the described process.

Despite being subject to a method according to this disclosure, proteins, which are smaller than microbes (including pathogens), are reduced to a lesser degree than are the microbes (including pathogens), which is important for preserving the initial beneficial properties and qualities of the liquid.

Methods and devices according to this disclosure have exhibited the full or partial reduction of microbes (including pathogens) in a liquid, including certain types of viruses (HIV, HCV, HSV and others). Following is an example of use of aspects of the invention on human blood plasma.

Example 1

| Temperature in ° C. of the blood plasma | Reduction factor (RF), $\log_{10}$ TCID$_{50}$ | | | | |
|---|---|---|---|---|---|
| exiting second vessel 20 | Herpes Simplex virus | Poliovirus | Adenovirus | Human Hepatitis C virus | Human Immunodeficiency virus |
| Test A | 60 | >4.7 | >6.4 | >4.18 | >4.3 | 3.7 |
| Test B | 58 | >4.7 | >6.4 | >4.18 | >4.3 | 2.66 |
| Test C | 56 | 3.2 | 5.0 | >4.18 | 2.56 | 2.58 |
| Test D | 54 | — | 3.0 | — | — | — |
| Test E | 52 | 1.8 | 1.5 | 1.98 | 1.3 | 1.58 |

In this example, human blood plasma was introduced in first vessel 70 (FIG. 2) and then subjected to a pressure of about 13.5 bar, which is about 12.5 bar above ambient pressure (which was about 1 bar). Compressed nitrogen from an outside source (a cylinder of compressed nitrogen) was used to add 0.00004-0.00006 pounds of nitrogen to about 0.13 liters of human blood plasma inside of first vessel 70. Then the blood plasma with inert gas was pumped to heat exchanger 80, where it was heated to 40° C.-48° C., depending upon the temperature of the blood plasma as it exited second vessel 20, as indicated above in Test A-Test E.

Afterwards, the heated blood plasma was introduced to the first end 11 of the nozzle 1 and subjected to a reduction in pressure as it went from about 12.5 bar at the first end 11 of nozzle 1 to about 1 bar as it exited second end 12 and was atomized into droplets in cavity 30. As the liquid droplets of blood plasma entered cavity 30 of second vessel 20 they were heated a total amount of about 10° C.-12° C., at a rate of about 4,000° C./sec, to a temperature of about 52° C.-60° C., as indicated above for Test A-Test E.

The treated blood plasma eventually exited cavity 30 through exit 31. Then the collected blood plasma was cooled at about 2° C./sec until the temperature of the blood plasma was about 8° C.

Despite being subject to the method, proteins, which are smaller than microbes (including pathogens), were practically not destroyed, which is important for preserving the initial desirable properties and qualities of blood plasma. Referring to Example 1, after treatment of the blood plasma the total protein concentration was reduced by from about 4.5% (i.e., 95.5% of the protein remained) at a temperature of about 54° C. of the blood plasma exiting the second vessel, to about 11.9% (i.e., 88.1% of the protein remained) at a temperature of about 60° C. of the blood plasma exiting the second vessel 20.

FURTHER ALTERNATE EMBODIMENTS

This disclosure also includes embodiments that do not use inert gas, but use only heat, rate of heating, pressure, and the rate of pressure drop, to reduce microbes (including pathogens) in a liquid. These embodiments may utilize any of the temperatures, rate of temperature increase, pressure, or rate of pressure drop, discussed previously in this specification. Any of the previously described equipment or method parameters may be utilized. Further, any suitable method steps or parameters that follow could be utilized with any of the above disclosed methods that utilize inert gas.

A method not utilizing inert gas would not require first vessel 70 because inert gas is not dissolved in the liquid under pressure. The liquid L could or could not be heated by heating heat exchanger 80 prior to being released into cavity 30 of vessel 20 and being subject to the pressure drop. Further, any suitable vessel other than vessel 20 could be utilized to perform a method according to these embodiments.

In one embodiment, the process preferably includes diffusing the liquid into droplets (the droplets may have an average diameter of about 100-200 μm, or about 30-500 μm in diameter) utilizing nozzle 1. There would be a pressure drop from first end 11 of nozzle 1 to when the liquid exits second end 12 (i.e., the nozzle outlet). Any suitable size or shape of droplets is sufficient, and the droplets may not be of the same size or shape. The speed of the droplets exiting second end 12 of nozzle 1 may be any suitable speed, including the speeds set forth previously or below.

The liquid may be heated prior to entering the nozzle 1, such as by using heat exchanger 80. The liquid may enter the first end of nozzle 1 at about 35° C. to 90° C., about 40° C. to about 80° C., or about 50° C. to about 70° C., or about 52° C. to 56° C., or up to about 75° C., or up to about 60° C., or up to about 65° C., or up to about 70° C., although prior to entering the inlet the liquid may be heated to any suitable temperature depending upon the liquid.

The liquid is also preferably heated after, or while, being subjected to the pressure drop in cavity 30, so that the temperature of the liquid is increased by any suitable amount, such as about 2.8° C. or more, about 5° C. or more, 10° C. or more, any temperature of about 2.8° C. to about 10° C., any temperature of about 10° C. to about 20° C., any temperature of about 20° C. to about 30° C., any temperature of about 20° C. to about 40° C., about 15° C. or more, about 20° C. or more, about 30° C. or more, or about 40° C. or more, or about 50° or more, or any suitable temperature increase, including those previously disclosed for the liquid L in cavity 30. The temperature to which the liquid is heated, before and/or after entering the second vessel 20, is selected based upon the type of liquid and microbes (including pathogens). The liquid is preferably not heated to a temperature at which the desirable qualities of the liquid are greatly diminished.

When the liquid temperature is increased, it is preferably increased to any suitable temperature, such as any temperature from about 35° C. to about 85° C., or any temperature of about 50° C. to about 75° C., or any temperature of about 62° C. to about 65° C., or about 70° C. or more, or about 75° C. or more, or 85° C. or more, or any suitable temperature, including the temperatures previously disclosed in this description.

Further, the rate of heating the liquid may be any amount from about 2° C./sec or greater, 1° C./sec to 5° C./sec, about one second to sixty seconds per 1° C., about 0.5° C. per second or less, about 1° C. per second, about 1° C. per ten seconds or more, or about 1° C. per second to about 10° C. per sixty seconds, or any suitable rate of heating, including the rates disclosed previously in this description. The liquid may be heated using any known device or method.

All or some of the heating may also be performed in whole or in part after the droplets have been collected to form a liquid volume. Heating a collected liquid volume, if done, can occur inside and/or outside of inner cavity 30 or at an outlet of the reactor, using any suitable device such as a heat exchanger. In one embodiment, the liquid L is partially heated in any desired manner while in droplet form and further heated in any desired manner after being collected into a liquid volume. For example, the liquid may be heated by about 2.8° C. while in droplet form and by about another 2.8° C. or more after it has been collected to form a liquid volume, or heated by about 2.8° C. or more in droplet form and about another 10° C. after being collected into a liquid volume, or heated about 10° C. in droplet form and about another 5° C. after being collected. Alternatively, the liquid may be completely heated in any suitable manner to the desired temperature while in droplet form, or entirely after it has been collected into a liquid volume.

The liquid may be heated in the inner cavity 30 due to the temperature maintained in the inner cavity 30, or by introducing stream, hot air, or another substance to heat the droplets.

Regardless of how the temperature of the liquid L is increased, the liquid can be maintained at that temperature for any desired time, and by any suitable method, after the liquid has been collected. The liquid may be maintained at the higher temperature to which it is raised for any suitable period, such as about 0.1 seconds to 1.0 seconds, 0.5 seconds or more, about one second or more, about two seconds or more, about five seconds or more, about ten seconds or more, about twenty seconds or more, about thirty seconds or more or more, about one minute or more, about two minutes or more, about five minutes or more, about ten minutes or more, about twenty minutes or more, about thirty minutes or more, or any timeframe of about 0.5 sec to about 30 minutes.

A pump may be used for increasing the pressure at the nozzle inlet 11, and a separate pump for regulating the pressure in the inner cavity 30. A second heat exchanger (not shown), may be positioned inside and/or outside of the inner cavity 30, to heat the liquid collected, and a pump (not shown) may be used to pump the collected liquid L out of second vessel 20. Further, inner cavity 30 may be heated as explained herein, by a heating jacket 3 on the outside of vessel 20, or other structures may be used to introduce one or more substances, such as steam or hot air, to heat the droplets exiting nozzle 1.

A suitable pressure drop is utilized to reduce microbes (including pathogens) in the liquid L. The pressure drop could be of any suitable amount, including any of the magnitude disclosed previously in this description. Or, the rate of pressure drop may be about $10^2$ Pa/sec or more, about $10^3$ Pa/sec or more, about $10^4$ Pa/sec or more, about $10^5$ Pa/sec or more, about $10^9$ Pa/sec or more, any rate from about $10^5$ Pa/sec to about $10^{10}$ Pa/sec, about eight bar per $\frac{1}{10{,}000}$ second or more, about eight bar per millisecond or more, about eight bar per $\frac{1}{100}$ second or more, eight Bars per $\frac{1}{10}$ second or more, about eight Bars per second or more, about eight Bars per two seconds or more, about eight Bars per five seconds or more, or about eight Bars per ten seconds or more.

After being subjected to the pressure drop, and optionally heated, the liquid L is preferably collected in one or more reservoirs in the inner cavity 30. There is preferably one reservoir at the bottom of second vessel 20, but there could be more than one reservoir at more than one location in second vessel 20. The collected liquid L may then be increased in temperature, or maintained at the same temperature, or cooled. The collected liquid, if heated, can be heated either in the inner cavity 3 and/or outside second vessel 20. The liquid L is preferably cooled, such as to a temperature, at a cooling rate, and in the same manner as previously disclosed.

Alternate Parameters for any of the Methods
Disclosed Herein

Any of the methods described above could be performed with the following operating parameters. For example, the total pressure drop could be 5 Bars or more, the total amount of temperature increase of the liquid could be 2.8° C. or more; the temperature of the liquid after its temperature is increased by 2.8° C. or more could be any amount from 35° C. to 85° C.; the average velocity of liquid droplets in the reactor can be any amount from about 5 m/sec or more, or 7.6 m/sec to about 14 m/sec, or about 10 m/sec or more, or about 9.1 m/sec; the dwell time of liquid droplets in the reactor after leaving the nozzle and contacting a surface could be any amount from 0.1 to 1.0 seconds, or about 0.4 seconds; and the average droplet diameter could be about 30-100 microns, or about 30-500 microns; and/or the total pressure drop can be from a high pressure of about 5 Bars or more to a lower pressure of about ½ to 1 Bar.

Following are non-limiting examples of this disclosure:

Example 1

A device for reducing the number of microbes (including pathogens) in a liquid, the device comprising:

(a) an inner cavity; and (b) a nozzle for diffusing a stream of liquid into droplets of liquid, the nozzle having an inlet into which the liquid enters and an outlet opening to the inner cavity and through which the liquid enters the inner cavity, the pressure of liquid at the inlet being at least eight Bars greater than the pressure at the outlet; and (c) after or as the liquid has been diffused into droplets, increasing its temperature by 10° C. or more.

Example 2

The device of example 1 wherein the nozzle is comprised of stainless steel.

Example 3

The device of example 1 wherein the inner cavity includes walls that are vertically oriented.

Example 4

The device of example 3 wherein the nozzle is centered between the walls.

Example 5

The device of any of examples 1-4 wherein the reactor has a top and the nozzle is at the top.

Example 6

The device of example 5 wherein the outlet is facing downward into the cavity.

Example 7

The device of example 3 wherein the interior walls are not parallel.

Example 8

The device of example 3 wherein the interior walls are parallel.

Example 9

The device of example 1 wherein the inner cavity is cylindrical.

Example 10

The device of example 1 wherein the inner cavity is conical.

Example 11

The device of example 10 wherein the inner cavity has a larger diameter at the bottom than at the top.

Example 12

The device of example 10 wherein the inner cavity has a smaller diameter at the bottom than at the top.

Example 13

The device of any of examples 1-12 wherein the inner cavity is divided into a plurality of compartments and at least one nozzle has an outlet opening to the inner cavity of one compartment.

Example 14

The device of example 13 wherein each nozzle is at the top of the reactor.

Example 15

The device of any of examples 1-14 that includes a plurality of nozzles.

Example 16

The device of any of examples 1-15 further comprising a reservoir at the bottom of the reactor to collect the droplets as a liquid volume.

Example 17

The device of example 16 wherein the liquid collected in the reservoir is heated so its temperature increases by about 10° C.

Example 18

The device of example 17 wherein the heating is performed without introducing a fluid or gas into the liquid.

Example 19

The device of examples 16 or 17 that further includes a heat exchanger to heat the liquid volume.

Example 20

The device of any of examples 17-19 wherein the liquid volume is heated while it is at least partially inside of the reactor.

Example 21

The device of any of examples 17-20 wherein the liquid volume is heated while it is at least partially outside of the reactor.

Example 22

The device of any of examples 17-21 wherein the liquid volume is heated to between 62° C. and 65° C.

Example 23

The device of any of examples 17-21 wherein the liquid volume is heated to between 48° C. and 82° C.

Example 24

The device of any of examples 17-21 wherein the liquid volume is heated to between 50° C. and 72° C.

Example 25

The device of any of examples 17-21 wherein the liquid volume is heated to 70° C. or less, or 75° C. or less.

Example 26

The device of any of examples 17-21 wherein the liquid volume is heated to a temperature below the pasteurization temperature of the liquid.

Example 27

The device of any of examples 1-25 wherein the liquid pressure changes at a rate of any amount from $10^5$ to $10^{10}$ Pa/sec.

Example 28

The device of any of examples 1-25 wherein the liquid pressure changes at a rate of $10^9$ Pa/sec or more.

Example 29

The device of any of examples 1-25 wherein the liquid pressure changes at a rate of $10^5$ Pa/sec or more.

Example 30

The device of any of examples 1-25 wherein the liquid pressure changes at a rate of eight Bars per millisecond or more.

Example 31

The device of any of examples 1-25 wherein the liquid pressure changes at a rate of eight Bars per $\frac{1}{100}$ of a second or more.

Example 32

The device of any of examples 1-25 wherein the liquid pressure changes at a rate of eight Bars per $\frac{1}{10}$ of a second or more.

Example 33

The device of any of examples 1-25 wherein the liquid pressure changes at a rate of eight Bars per second or more, or eight bars per two seconds or more, or eight bars per five seconds or more, or eight bars per ten seconds or more, or eight bars per thirty seconds or more, or eight bars per minute or more.

Example 34

The device of any of examples 1-33 wherein the liquid spray exiting the nozzle is in droplets of an average size of 100-200 microns in diameter or less, or 100-400 microns in diameter, or 30 to 500 microns in diameter.

Example 35

The device of any of examples 1-34 wherein the speed of the liquid droplets exiting the outlet is 5 m/sec or more.

Example 36

The device of any of examples 1-35 wherein the liquid is heated before entering the nozzle inlet

Example 37

The device of any of examples 1-36 wherein the heating rate of the liquid is about 1100° C./sec or more.

Example 38

The device of any of examples 1-36 wherein the heating rate of the liquid is between 1° C. and 5° C. per second, or about 1100° C./sec, or 1° C./sec or is any amount from about 0.5° C. per second or more, or about 2° C./sec to 15,000° C./sec, or about 2° C./sec or more.

Example 39

The device of any of examples 1-38 that includes a pump for increasing the pressure of the fluid at the inlet to the nozzle.

Example 40

The device of any of examples 1-39 wherein the nozzle comprises a cavity, a nozzle in fluid communication with the cavity, the nozzle for creating a flat spray from a cylindrical or conical stream of liquid, a vacuum control unit in communication with the cavity, wherein the vacuum control unit and nozzle create a pressure change in the liquid product entering the inner cavity.

Example 41

The device of any of examples 1-40 wherein the temperature of the liquid entering the nozzle is from 52° C. and 56° C., or from 40° C. and 60° C., or from 45° C. and 80° C., or from 40° C. and 70° C., or 75° C. or less, or from 30° C. to 90° C.

Example 42

The device of any of examples 1-41 wherein the nozzle includes an inlet, a central portion and an outlet offset at a 45°-90° angle from the inlet.

Example 43

The device of examples 1-42 wherein the nozzle includes an interior structure that comprises a flat plate that converts a generally cylindrical stream of liquid into a flat spray.

Example 44

The device of any of examples 1-43 that further includes a first heat exchanger to increase the temperature of the liquid before it reaches the nozzle inlet.

Example 45

The device of any of examples 1-44 that that further includes a second heat exchanger to increase the temperature of the volume of liquid, after the volume of liquid is collected in the reservoir of the reactor.

Example 46

The device of example 45 wherein the second heat exchanger is positioned partially or entirely within the inner cavity of the reactor.

Example 47

The device of example 45 wherein the second heat exchanger is positioned partially or entirely outside of the reactor.

Example 48

The device of any of examples 1-47 that includes a heater for heating the inner cavity of the reactor.

Example 49

The device of example 48 wherein the heater does not introduce heated gas or liquid into the inner cavity.

Example 50

The device of examples 48 or 49 wherein the heater maintains the inner cavity at a temperature higher than the temperature of the liquid at the nozzle inlet.

Example 51

The device of any of examples 13-15 wherein the nozzles are positioned such that droplets exiting the respective nozzles do not overlap.

Example 52

The device of any of examples 1-15 wherein each nozzle creates a conical spray of droplets exiting the nozzle outlet.

Example 53

The device of any of examples 1-52 that further includes a sump beneath the reservoir.

Example 54

The device of any of examples 1-53 wherein the inner cavity has one or more walls comprised of stainless steel.

Example 55

The device of any examples 1-54 wherein the inner cavity has no raised or depressed internal seams, and the seams are flush with the inner cavity wall.

Example 56

The device of any of examples 1-17, or 19-55 that includes one or more second nozzles for introducing one or more of air, steam or another substrate into the cavity to heat the droplets.

Example 57

The device of any of examples 1-56 that includes a pump for pumping liquid into the reactor.

Example 58

A process for reducing the number of microbes (including pathogens) in a liquid, the process including the steps of:
(a) diffusing the liquid into liquid droplets as the liquid is subject to at least a five Bars pressure; and
(b) after the liquid is diffused, heating the liquid to increase its temperature by 2.8° C. or more.

Example 59

The process of example 58 wherein there is a nozzle outlet positioned in the inner cavity of a reactor.

Example 60

The process of examples 58 or 59 wherein there is a nozzle inlet and the liquid is pressurized at the nozzle inlet.

Example 61

The process of any of examples 58-60 wherein the liquid is converted from a cylindrical or conical stream into a flat spray of droplets.

Example 62

The process of example 60 wherein at least an eight Bar pressure drop occurs from the nozzle inlet to the nozzle outlet.

Example 63

The process of any of examples 58-62 wherein the speed of pressure change in the liquid product is approximately $10^5$ Pa/sec or more, or any amount from $10^5$ Pa/sec to $10^{10}$ Pa/sec, or eight Bars per millisecond or more, or eight Bars per $\frac{1}{100}$ second or more, or eight Bars per $\frac{1}{10}$ second or more, or eight Bars per second or more, or eight Bars per two seconds or more, eight Bars per five seconds or more, or eight Bars per ten seconds or more.

Example 64

The process of any of examples 58-63 wherein the speed of the droplets exiting the nozzle outlet is about 5 m/sec or more, or 10 m/sec or more.

Example 65

The process of any of examples 58-64 wherein step of heating the liquid by 2.8° C. or more is performed at a pressure of 0.25 Bar to 1 Bar.

Example 66

The process of any of examples 58-65 wherein the heating rate of the liquid product does not exceed 1100° C./sec, or 1° C. to 5° C. per second, 0.5° C. per second, or 1° C. per second to 10° C. per ten seconds, or 1° C. per second to 10° C. per sixty seconds, or 2° C./sec or more.

Example 67

The process of any of examples 58-66 wherein the microbe is selected from one or more of the group consisting of: (a) one or more bacteria or other pathogens, (b) one or more viruses, and (c) one or more fungi.

Example 68

The process of any of examples 58-67 wherein the liquid droplets are heated to increase their temperature by 2.8° C. or more.

Example 69

The process of any of examples 58-68 wherein the liquid droplets are collected to form a liquid volume and the liquid volume is heated to increase its temperature by 2.8° C. or more.

Example 70

The process of any of examples 1-69, wherein the liquid is one of: water, milk, other dairy products, fruit juice (such as orange juice), coconut milk, coconut water, coconut cream, beer, wine, a blood product, blood plasma, a biological product, coconut milk, a liquid food product, a pharmaceutical, a biological product, precursors for making a pharmaceutical, albumin, immunoglobulin, bovine colostrum, serums, culture media, vegetable juice, brewer's wort, and wine base.

Example 71

The process of any of examples 59-70 wherein the nozzle has an outlet with a diameter of between 1 mm and 30 mm or between 1 mm and 3 mm.

Example 72

The process of any of examples 58-68 wherein the liquid is increased in temperature by 2.8° C. or more partially while it is in the droplet phase and partially after it has been collected into a liquid volume.

Example 73

The process of any of examples 58-72 wherein the liquid is heated prior to entering the nozzle.

Example 74

The process of any of examples 58-73 wherein the temperature of the liquid is increased by at least 2.8° C. to between 35° C. and 85° C.

Example 75

The process of any of examples 58-73 wherein the temperature of the volume of liquid is increased by at least 2.8° C. to between 50° C. and 75° C., or between 60° C.-65° C. or to 70° C. or less, or to 75° C. or less, or to 35° C. to 85° C., or to 85° C. or more.

Example 76

The process of any of examples 58-73 wherein the temperature of the liquid is increased after diffusion to below the pasteurization temperature of the liquid.

Example 77

The process of any of examples 58-76 wherein the diameter of the liquid droplets average 100-200 microns or 100-400 microns or less, or 30 microns to 500 microns.

Example 78

The process of any of examples 58-77 wherein the liquid is heated to between 52° C. and 56° C. before being diffused into droplets.

Example 79

The process of any of examples 58-78 wherein the liquid is maintained at the temperature increased by 2.8° C. or more for 0.5-10 seconds.

Example 80

The process of any of examples 58-79 wherein eight Bars means 8.0 Bars.

Example 81

The process of any of examples 58-79 wherein eight Bars means at least 7.95 Bars.

Example 82

The process of any of examples 58-79 wherein eight Bars means at least 7.6 Bars.

Example 83

The process of any of examples 58-79 wherein 10° C. means at least 9.8° C.

Example 84

The process of any of examples 58-62 or 64-83 wherein the speed of the pressure drop is either $10^2$ Pa/sec or more, $10^3$ Pa/sec or more, $10^4$ Pa/sec or more, $10^5$ Pa/sec or more, $10^9$ Pa/sec or more, eight Bars per $\frac{1}{10,000}$ second or more, eight Bars per $\frac{1}{1,000}$ second or more, eight Bars per $\frac{1}{100}$ second or more, eight Bars per $\frac{1}{100}$ second or more, eight Bars per $\frac{1}{10}$ second or more, eight Bars per second or more, eight bars per two seconds or more, eight Bars per five seconds or more, eight Bars per ten seconds or more, eight Bars per thirty seconds or more, eight Bars for sixty seconds or more, or between eight Bars per millisecond and eight Bars per second.

Example 85

The process of any of examples 58-84 wherein the liquid is heated by at least 2.8° C. while in the droplet phase and at least another 2.8° C. after being collected as a liquid volume.

Example 86

The process of any of examples 58-85 wherein the liquid is maintained at the increased temperature of 2.8° C. or more for either at least ½ second, at least one second, at least two seconds, at least one to five seconds, at least five seconds, at least five to ten seconds, at least ten seconds, at least twenty seconds, at least thirty seconds, at least one minute, or at least five minutes, or at least ten minutes, or at least twenty minutes, or at least thirty minutes.

Example 87

The process of any of examples 58-86 wherein the liquid volume is pumped out of the reactor before it is heated to an increased temperature of 2.8° C. or more.

Example 88

The device of any of examples 1-57 wherein the reservoir tilts downward at an angle to permit easier removal of the liquid volume.

Example 89

The process or device of any of examples 1-88, wherein the total pressure drop is 5 Bars or more,

Example 90

The process or device of any of examples 1-89, wherein the total amount of temperature increase of the liquid is 2.8° C. or more.

Example 91

The process or device of example 90, wherein the temperature of the liquid after its temperature is increased by 2.8° C. or more is any amount from 35° C. to 85° C., or 85° C. or more.

Example 92

The process or device of any of examples 1-91, wherein the average velocity of liquid droplets in the reactor after being diffused is any amount from about 7.6 m/sec to about 14 m/sec.

Example 93

The process or device of any of examples 1-91, wherein the average velocity of liquid droplets in the reactor is about 5 m/sec or more.

Example 94

The process or device of any of examples 1-91, wherein the average velocity of the liquid droplets in the reactor is about 9.1 m/sec.

Example 95

The process or device of any of examples 1-94, wherein the dwell time of liquid droplets in the reactor after leaving the nozzle and contacting a surface or liquid volume is any amount from 0.1 to 1.0 seconds.

Example 96

The process or device of example 95, wherein the dwell time of liquid droplets in the reactor is about 0.4 seconds

Example 97

The process or device of any of examples 1-96, wherein the average liquid droplet diameter is about 30-100 microns.

Example 98

The process or device of any of examples 1-96, wherein the average liquid droplet diameter is about 30-500 microns.

Example 99

The process or device of any of examples 1-98, wherein the total pressure drop is from about 5 Bar or more to about ½ to 1 Bar.

Example 100

The process or device of any of examples 1-99, wherein the temperature of the liquid after being heated is from 35° C. to 90° C.

Example 101

The process or device of any of examples 1-100, wherein the temperature of the liquid is increased at a rate from 2° C./sec or more.

Example 102

The process or device of any of examples 1-101, wherein the average velocity of the liquid droplets inside of the reactor is 5 m/sec or more.

Example 103

The process or device of any of examples 1-102, wherein the pressure drop and temperature increase begin at the same time.

Example 104

The process or device of any of examples 1-102, wherein the pressure drop begins before the temperature increase begins.

Example 105

The process or device of any of examples 1-104, wherein a first pressure (before the pressure drop) is 5 Bars or more and the pressure (the second pressure) after the pressure drop is ½ Bar to 1 Bar.

Example 106

The process or device of any of examples 1-105, wherein the pressure of the liquid is dropped from 5 Bars or more to a pressure above the steam table pressure of the temperature inside of the reactor.

Some further non-limiting examples of the disclosure follow:

Example 1

A method of reducing the number of microbes (including pathogens) in a liquid, the method comprising the steps of:
a. introducing the liquid into a first vessel;
b. introducing inert gas into the first vessel;
c. raising the pressure in the first vessel to a first pressure that is greater than 1 bar, and at which at least some of the introduced inert gas dissolves into the liquid; and
d. introducing the liquid into a second vessel at a second pressure, wherein the second pressure is less than the first pressure, and at least some of the inert gas is released from the liquid at the second pressure.

Example 2

The method of any of example 1, wherein there is a nozzle with a first end and a second end, and that further includes the step of the liquid entering the first end of the nozzle after it leaves the first vessel, and exiting the second end of the nozzle and being introduced into the second vessel.

Example 3

The method of example 1 or 2, wherein the step of raising the pressure to the first pressure occurs as the inert gas enters the first vessel.

Example 4

The method of any of examples 1-3, wherein the first pressure is two times or more greater than the second pressure.

Example 5

The method of any of examples 1-3, wherein the first pressure is three times or more greater than the second pressure.

Example 6

The method of any of examples 1-3, wherein the first pressure is four times or more greater than the second pressure.

Example 7

The method of any of examples 1-3, wherein the first pressure is five times or more greater than the second pressure.

Example 8

The method of any of examples 1-3, wherein the first pressure is six times or more greater than the second pressure.

Example 9

The method of any of examples 1-3, wherein the first pressure is seven times or more greater than the second pressure.

Example 10

The method of any of examples 1-3, wherein the first pressure is eight times or more greater than the second pressure.

Example 11

The method of any of examples 1-3, wherein the first pressure is nine times or more greater than the second pressure.

Example 12

The method of any of examples 1-3, wherein the first pressure is ten times or more greater than the second pressure.

Example 13

The method of any of examples 1-3, wherein the first pressure is about 10 bar and the second pressure is about 1 bar.

Example 14

The method of any of examples 1-3 that further includes the step of heating the liquid, while it is in the first vessel.

Example 15

The method of any of examples 1-14 that further includes the step of heating the liquid when it is in the second vessel.

Example 16

The method of any of examples 1-14 that further includes the step of heating the liquid to about 40° C.-58° C. before it enters the second vessel.

Example 17

The method of example 16 that further includes the step of heating the liquid when it is in the second vessel.

Example 18

The method of any of examples 1-3 or 14-17, in which the first pressure is sufficient to increase the weight amount of inert gas dissolved in the liquid in the first vessel by a factor of about two or more as compared to the weight amount of inert gas dissolved in the liquid in the first vessel at 1 bar.

Example 19

The method of any of examples 1-18 that further includes the step of collecting the liquid inside of the second vessel.

Example 20

The method of example 19 that further includes the step of cooling the liquid after it has been collected.

Example 21

The method of example 20, wherein the liquid is cooled at a rate of about 1° C.-5° C. per second, or about 2° C. per second, or any amount from 0.1 C/sec to 20° C./sec.

Example 22

The method of example 20 or example 21, wherein the liquid is cooled outside of the second vessel.

Example 23

The method of any of examples 1-22, wherein the inert gas is nitrogen.

Example 24

The method of any of examples 1-23, wherein the liquid is selected from one of the group consisting of: water, a blood product, blood plasma, a biological product, milk, fruit juice, coconut milk, liquid food, a pharmaceutical, biological products, a precursor of a biological product, albumin, immunoglobulin, bovine colostrum, serum, culture media, vegetable juice, coconut water, brewer's wort, and wine base.

Example 25

The method of any of examples 1-24, wherein a second end of the nozzle is positioned in an inner cavity of the second vessel.

Example 26

The method of any of examples 1-25, wherein the liquid is pressurized at a first end of the nozzle.

Example 27

The method of example 2, wherein the liquid is subject to about a ten bar or greater pressure drop from the first end of the nozzle and the position at which the liquid exits the second end of the nozzle.

Example 28

The method of example 1 or example 2, wherein the liquid is heated while in the first vessel.

Example 29

The method of example 28, wherein the liquid is heated in the first vessel to a temperature of about 50° C. less, or lower, than the temperature to which the liquid is raised while in the second vessel.

Example 30

The method of example 2, wherein the liquid is subject to about a 5 Bar or greater pressure drop occurs from the first end of the nozzle and the position at which the liquid exits the second end of the nozzle.

Example 31

The method of example 15 or example 17, wherein the liquid is heated at a rate of about 3,000° C./sec to about 5,000° C./sec in the second vessel.

Example 32

The method of any of examples 1-31 that further includes the step of dropping the pressure of the liquid at a rate of between 1 Bar/sec to 10,000 bar/sec as the liquid is introduced into the second vessel.

Example 33

The method of any of examples 2-32, wherein if the nozzle is utilized, the speed of the liquid exiting the second end of the nozzle is about 5 m/sec or more.

Example 34

The method of any of examples 2-33, wherein if the nozzle is utilized, the liquid is heated by a total amount of 2.8° C. or more inside the second vessel.

Example 35

The method of any of examples 2-34, wherein the nozzle has an outlet with a diameter of between 0.2 mm and 20 mm.

Example 36

The method of any of examples 1-35, wherein the temperature of the liquid is increased in the second vessel to between about 35° C. and about 85° C.

Example 37

The method of any of examples 1-36 that further includes the step of heating the liquid after it exits the first vessel and before it enters the second vessel.

Example 38

The method of any of examples 1-37 that further includes the step of cooling the liquid after it has left the second vessel.

Example 39

The method of any of examples 1-38 that further includes the step of equalizing the pressure between the outside and inside of the second vessel.

Example 40

The method of any of examples 1-39, wherein the step of raising the pressure to the first level occurs before the inert gas enters the first vessel.

Example 41

The method of any of examples 2-40, wherein a first end of the nozzle is positioned outside of an inner cavity of the second vessel.

Example 42

The method of any of examples 2-41, wherein the liquid enters a first end of the nozzle and is atomized into droplets as it exits a second end of the nozzle and enters an inner cavity of the second vessel.

Example 43

The method of any of examples 1-42, wherein the pressure inside of the second vessel is about ½ Bar to 1 bar.

Example 44

The method of any of examples 2-43, wherein the liquid exits the nozzle as droplets.

Example 45

The method of any of examples 1-44, wherein the first pressure is about 5 bars or greater than the second pressure.

Example 46

The method of example 47, wherein the liquid is heated to a temperature of about 50° C. less, or lower, to the temperature to which the liquid is raised in the second vessel.

Example 47

The method of any of examples 1-46, wherein the liquid is heated by a total amount of 2.8° C. or more inside the second vessel.

Example 48

The method of example 26, wherein the liquid is at the first pressure when it is at the first end of the nozzle.

Example 49

The method of any of examples 1-2 or 4-48 that includes the step of raising the pressure to the first pressure before the inert gas enters the first vessel.

Example 50

The method of any of examples 1-2 or 4-48 that includes the step of raising the pressure to the first pressure after the inert gas enters the first vessel.

Example 51

The method of any of examples 1-50 that further includes the step of equalizing the pressure between the inside and outside of the second vessel.

Example 52

The method of any of examples 1-51 that further includes the step of creating a lower pressure in the liquid prior to introducing it into the first vessel.

Example 53

The method of any of examples 1-52, wherein the liquid is introduced into the first vessel by pumping it into the first vessel implemented with a pump.

Example 54

The method of any of examples 1-53, wherein the liquid is moved out of the first vessel before being introduced into the second vessel.

Example 55

The method of example 54, wherein the liquid is moved out of the first vessel by a pump.

Example 56

The method of any of examples 1-55, wherein the temperature of the liquid in the first vessel is about equal to the temperature of a room in which the first vessel is located.

Example 57

The method of any of examples 1-56 that further comprises the step of cooling the liquid prior to introducing it into the first vessel.

Example 58

The method of any of examples 1-56 that further includes the step of heating the liquid prior to introducing it into the first vessel.

Example 59

The method of any of examples 56-58, wherein the room temperature is about 17° C. to about 26° C.

Example 60

The method of any of examples 1-59, wherein the inert gas is introduced into the first vessel at a greater pressure than the first vessel.

Example 61

The method of any of examples 1-60, wherein the first pressure is selected based upon the type of liquid and type(s) of microbe(s) (including pathogens).

Example 62

The method of any of examples 1-61, wherein the liquid is bovine colostrum and the first pressure is about 9 bar or greater.

Example 63

The method of any of examples 1-62, wherein the liquid is not heated to a temperature that negatively affects the quality of the liquid.

Example 64

The method of any of examples 1-61 or 63, wherein the liquid is human blood plasma that is heated to about 37° C. to about 48° C. before being introduced into the second vessel.

Example 65

The method of any of examples 1-63, wherein the liquid is bovine colostrum that is heated to about 40° C. to about 60° C. before being introduced into the second vessel.

Example 66

The method of any of examples 1-65, wherein the second pressure is 1 Bar or lower.

Example 67

The method of any of examples 1-66, wherein the second vessel has a frustoconical top part having an inner wall, and a cylindrical center part.

Example 68

The method of example 67, wherein the second vessel has a frustoconical lower part.

Example 69

The method of any of examples 67-68 that includes the step of spraying the liquid with dissolved gas into the second vessel so that the sprayed liquid does not contact the inner wall of the frustoconical top part of the second vessel.

Example 70

The method of example 64 in which the human blood plasma with dissolved inert gas is sprayed as droplets into the second vessel and an average droplet diameter is about 30-150 micrometers.

Example 71

The method of example 62 or example 65, in which the bovine colostrum is sprayed as droplets into the second vessel and an average droplet diameter is about 150-300 micrometers.

Example 72

The method of any of examples 2-71, wherein a velocity of droplets exiting the nozzle may be about 5 m/sec or more, 40 m/sec or less, or about 40 m/sec or more.

Example 73

The method of any of examples 1-61, 63-64, 67-70, or 72, wherein the liquid is human blood plasma that is heated to about 45° C. to 60° C. in the second vessel.

Example 74

The method of example 1-63, 65-69, or 71, wherein the liquid is bovine colostrum that is heated to about 55° C. to 80° C. in the second vessel.

Example 75

The method of any of examples 1-74, in which the rate of heating the liquid in the second vessel is any suitable rate of 500° C./sec to 7000° C./sec, or 2° C. or more.

Example 76

The method of any of examples 19-61, 63-64, 67-70, 72-73, or 75, wherein the liquid is human blood plasma that is cooled to 8° C. or lower after it is collected.

Example 77

The method of any of examples 18-61, 63, 66-69, 72, or 75, wherein the liquid is orange juice that is cooled to 25° C. or lower after it is collected.

Example 78

The method of any of examples 52-77 that includes the step of lowering the pressure of the liquid to 1 bar or lower before it enters the first vessel.

Example 79

The method of example 57, wherein the liquid is cooled to about the temperature of the room in which the first vessel is located.

Example 80

The method of example 58, wherein the liquid is heated to about the temperature of the room in which the first vessel is located.

Example 81

The method of any of examples 1-17 or 19-80, in which the first pressure is sufficient to increase the weight amount of inert gas dissolved in the liquid in the first vessel by a factor of three or more as compared to the weight amount of inert gas dissolved in the liquid in the first vessel at atmospheric pressure.

Example 82

The method of any of examples 1-17 or 19-80, in which the first pressure is sufficient to increase the weight amount of inert gas dissolved in the liquid in the first vessel by a factor of five or more as compared to the weight amount of inert gas dissolved in the liquid in the first vessel at atmospheric pressure.

Example 83

The method of any of examples 1-17 or 19-80, in which the first pressure is sufficient to increase the weight amount of inert gas dissolved in the liquid in the first vessel by a factor of seven or more as compared to the weight amount of inert gas dissolved in the liquid in the first vessel at atmospheric pressure.

Example 84

The method of any of examples 1-59 or 61-83, wherein the inert gas is introduced into the first vessel at a greater pressure than the first pressure.

Example 85

The method of any of examples 1-84, wherein the first vessel and second vessel are not connected.

Example 86

The method of any of examples 1-85, wherein the liquid is heated in a heating exchanger after it leaves the first vessel and before it enters the second vessel.

Example 87

The method of any of examples 19-86 that further includes the step of removing the collected liquid from the second vessel.

Example 88

The method of any of examples 19-87, wherein the collected liquid is cooled outside of the second vessel.

Example 89

The method of example 88, wherein the collected liquid is cooled by a cooling heat exchanger.

Example 90

The method of any of examples 1-89, wherein the liquid is subject to a pressure drop as it enters the second vessel and the pressure drop is either (a) about two or more bar, (b) about three or more bar, (c) about four or more bar, (d) about five or more bar, (e) about six or more bar, (f) about seven or more bar, (g) about eight or more bar, (h) about nine or more bar, (i) about ten bar or more, (j) about eleven bar or more, (k) about twelve bar or more, (1) about thirteen bar or more, (m) about 13.5 bar or more, or (n) about 15 bar or more.

Example 91

A method for reducing the microbes (including pathogens) in a liquid, the method comprising the steps of:
a. dissolving an inert gas into the liquid at a first pressure that is greater than 1 bar; and
b. introducing the liquid into a second vessel at a second pressure, wherein the second pressure is less than the first pressure, and inert gas is released from the liquid at the second pressure.

Example 92

The method of example 91 that further includes one or more of the parameters, steps, or devices of any one or more of examples 1-90.

Example 93

A method for reducing the microbes (including pathogens) in a liquid, the method comprising the steps of:
a. heating the liquid to a temperate of 50° C. or less than a temperature of the liquid and when it exits a second vessel;
b. introducing the liquid into a second vessel and heating it by 5° C. or more.

Example 94

The method of example 93, wherein the liquid is heated by 10° C. or more in the second vessel.

Example 95

The method of example 93 or 94 that further includes one or more of the parameters, steps, or structures of any one or more of examples 1-90.

Example 96

A method of reducing the microbes (including pathogens) in a liquid, the method comprising the steps of:
a. pressurizing the liquid to a first pressure greater than 1 bar; and
b. introducing the liquid into a second vessel at a second pressure, wherein the second pressure is less than the first pressure.

Example 97

The method of example 96 that further includes one or more of the parameters, steps, or structures of any one or more of examples 1-90.

Example 98

The method of any of examples 1-92, wherein some inert gas is in the liquid when the liquid is at the second pressure.

Example 99

The method of any of examples 1-98, wherein the total pressure drop is 5 Bars or more.

Example 100

The method of any of examples 1-99, wherein the total amount of temperature increase of the liquid is 2.8° C. or more.

Example 101

The method ice of example 100, wherein the temperature of the liquid after its temperature is increased by 2.8° C. or more is any amount from 35° C. to 90° C.

Example 102

The method of any of examples 1-101, wherein the average velocity of liquid droplets in the reactor is any amount from about 7.6 m/sec to about 14 m/sec, or 5 m/sec or more.

Example 103

The method of any of examples 1-101, wherein the average velocity of droplets in the reactor is about 10 m/sec or more.

Example 104

The method of any of examples 1-101, wherein the average velocity of the droplets in the reactor is about 9.1 m/sec.

Example 105

The method of any of examples 1-104, wherein the dwell time of liquid droplets in the reactor after leaving the nozzle and contacting a surface or a liquid volume is any amount from 0.1 to 1.0 seconds.

Example 106

The method of example 105, wherein the dwell time of liquid droplets in the reactor is about 0.4 seconds

Example 107

The method of any of examples 1-106, wherein the average liquid droplet diameter immediately after leaving the nozzle is about 30-100 microns.

Example 108

The method of any of examples 1-106, wherein the average liquid droplet diameter immediately after leaving the nozzle is about 30-500 microns.

Example 109

The method of any of examples 1-108, wherein the total pressure drop is from about 5 Bar or more to about ½ to 1 Bar.

Example 110

The process or device of any of examples 1-109, wherein the temperature of the liquid entering the nozzle is from 35° C. to 90° C.

Example 111

The process or device of any of examples 1-110, wherein the temperature of the liquid is increased at a rate of 2° C./sec or more.

Example 112

The process or device of any of examples 1-111, wherein the average velocity of the liquid droplets inside of the reactor is 5 m/sec or more.

Example 113

The process or device of any of examples 1-112, wherein the pressure drop and temperate increase begin at the same time.

Example 114

The process or device of any of examples 1-112, wherein the pressure drop begins before the temperature increase begins.

Example 115

The process or device of any of examples 1-114, wherein the first pressure (before the pressure drop) is 5 Bars or more and the second pressure (after the pressure drop) is ½ Bar to 1 Bar.

Example 116

The process or device of any of examples 1-115, wherein the pressure of the liquid is dropped from 5 Bars or more to a pressure above the steam table pressure of the temperature inside of the reactor.

Other methods and devices may be utilized that do not include the use of inert gas, first vessel 70, and possibly not heat exchanger 80. At least some types of microbes (including pathogens) can be reduced by using second vessel 20, potentially with one or more of heat exchanger 80 and heat exchanger 90.

Steps according to the methods herein may be performed in any order suitable to achieve a desired end product. The liquid is heated to appropriate temperatures for each liquid, those temperatures known to those skilled in the art. Additionally, after treatment utilizing a device and method according to the invention, the treated liquid may be treated a second time using any suitable device and method.

The present invention has been described above with reference to a number of exemplary embodiments and examples. The particular embodiments shown and described herein are illustrative of the exemplary embodiments, and are not intended to limit the scope of the invention. Changes and modifications may be made to the embodiments described herein without departing from the scope of the present invention. These and other changes or modifications are intended to be included within the scope of the claimed invention and the legal equivalents thereof.

What is claimed is:
1. A method for treating a liquid, the method comprising:
  (a) diffusing a liquid into droplets in an inner cavity of a reactor;
  (b) subjecting the liquid to a pressure drop of five Bars or more;

(c) increasing the temperature of the droplets by at least 2.8° C. in a first heating step;

(d) collecting the droplets to create a volume of liquid in a reservoir in the inner cavity, wherein the droplets are not mixed with steam; and (e) increasing the temperature of the volume of liquid by at least 2.8° C. in a second heating step.

2. The method of claim 1, wherein the liquid is diffused into droplets by at least one nozzle.

3. The method of claim 2, wherein the at least one nozzle has an inlet and an outlet and the pressure of the liquid is at least five Bars higher at the inlet than at the outlet.

4. The method of claim 3, further comprising increasing the pressure of the liquid at the inlet using a first pump.

5. The method of claim 1, wherein the liquid is increased in temperature by the at least 2.8° C. while it is being diffused into droplets.

6. The method of claim 1, further comprising transporting the volume of liquid outside of the reactor using a pump.

7. The method of claim 1, wherein increasing the temperature of the droplets is accomplished by subjecting the droplets to a suitable temperature inside of the inner cavity of the reactor.

8. The method of claim 1, further comprising step of transporting the volume of liquid outside of the reactor and increasing the temperature of the volume of liquid by the at least 2.8° C. while the volume of liquid is at least partially outside of the reactor.

9. The method of claim 1, wherein the temperature of the volume of liquid is increased by the at least 2.8° C. while the volume of liquid is entirely in the reactor.

10. The method of claim 1, wherein the temperature of the liquid is from 35° C. to 85° C. after being increased by the at least 2.8° C.

11. The method of claim 1, wherein the temperature of the liquid is increased at a rate of 2° C./sec or more.

12. The method of claim 1 that further includes a step of dropping the pressure at a rate selected from one of the group consisting of: any amount from $10^5$ to $10^{10}$ Pa/sec; $10^{10}$ Pa/sec or more; $10^5$ Pa/sec or more; eight bars per millisecond or more; eight bars per 1/10,000 second or more; eight bars per 1/100 second or more; eight bars per 1/10 second or more; eight bars per second or more, and eight bars per two seconds or more.

13. The method of claim 4, wherein the liquid is diffused into droplets as it exits a nozzle and the average velocity of the liquid droplets inside of the reactor is 5 m/sec or more.

14. The method of claim 1 that further includes a step of heating the liquid before it is diffused, wherein the liquid is heated to between 35° C. and 90° C. before being diffused.

15. The method of claim 1, further comprises a step of cooling the liquid to 8° C. to 25° C.

16. The method of claim 1, wherein the liquid is selected from one of the group consisting of: water, a blood product, blood plasma, a biological product, milk, fruit juice, coconut milk, liquid food, a pharmaceutical, biological products, a precursor of a biological product, albumin, immunoglobulin, bovine colostrum, serum, culture media, vegetable juice, coconut water, brewer's wort, and wine base.

17. The method of claim 2, wherein the velocity of the liquid droplets exiting the nozzle is 5 m/sec or more.

18. The method of claim 1, wherein the pressure drop and temperature increase begin simultaneously.

19. The method of claim 1, wherein the temperature increase begins after the pressure drop begins.

20. The method of claim 1 that is performed in a reactor and the dwell time of the liquid droplets in the reactor is 0.1 seconds to 1.0 seconds.

21. The method of claim 1, wherein the droplets have an average droplet diameter of 30-500 microns immediately after the liquid is diffused.

22. The method of claim 1 that further includes the step of introducing an inert gas into the liquid prior to the pressure drop of 5 Bars or more.

23. The method of claim 1 that has a first pressure of about 5 Bars or more prior to the pressure drop, and a second pressure of about ½ to 1 Bar after the pressure drop.

24. The method of claim 1, wherein the liquid is heated to any amount from about 35° C. to 85° C. after being increased in temperature by the at least 2.8° C.

25. The method of claim 22, wherein the liquid comprises a first pressure before subjecting the liquid to a pressure drop of five Bars or more, in which the first pressure is sufficient to increase the weight of inert gas in the liquid by a factor of two or more as compared to the weight of inert gas that would be in the liquid at one Bar.

26. The method of claim 4, wherein after the pressure drop the pressure is greater than the steam table pressure for the liquid at the temperature inside of the reactor.

* * * * *